(12) United States Patent
Bulleit et al.

(10) Patent No.: US 12,232,549 B1
(45) Date of Patent: *Feb. 25, 2025

(54) CUSTOMIZED PROTECTIVE DEVICES AND SYSTEMS AND METHODS FOR PRODUCING THE SAME

(71) Applicant: Protect3d, Inc., Durham, NC (US)

(72) Inventors: Clark Harrison Bulleit, Tampa, FL (US); Kevin Andrew Gehsmann, Greensboro, NC (US); Timothy John Skapek, Dallas, TX (US)

(73) Assignee: PROTECT3D INC., Durham, NC (US)

( * ) Notice: Subject to any disclaimer, the term of this patent is extended or adjusted under 35 U.S.C. 154(b) by 612 days.

This patent is subject to a terminal disclaimer.

(21) Appl. No.: 17/505,171

(22) Filed: Oct. 19, 2021

Related U.S. Application Data

(63) Continuation-in-part of application No. 17/037,166, filed on Sep. 29, 2020, now Pat. No. 11,882,888.
(Continued)

(51) Int. Cl.
*A41D 13/05* (2006.01)
*A61F 5/058* (2006.01)
(Continued)

(52) U.S. Cl.
CPC .......... *A41D 13/0512* (2013.01); *A63B 71/12* (2013.01)

(58) Field of Classification Search
CPC ............. A41D 13/0512; A61F 5/05808; A61F 5/10; A61F 13/066; A61F 13/143; A61F 5/058;
(Continued)

(56) References Cited

U.S. PATENT DOCUMENTS 1,850,540 A  12/1930  Erickson
2,377,339 A   6/1945  Greene
(Continued)

FOREIGN PATENT DOCUMENTS

CN      306074538      9/2020

OTHER PUBLICATIONS

Wall Street Journal. How Two Duke Benchwarmers and a 3-D Printer Rescued a Top NFL Quarterback Prospect. Mar. 1, 2019. https://www.wsj.com/articles/how-two-duke-benchwarmers-and-a-3-d-printer-rescued-a-top-nfl-quarterback-prospect-11551446283 (Year: 2019).
(Continued)

*Primary Examiner* — Tarla R Patel
(74) *Attorney, Agent, or Firm* — Husch Blackwell LLP; Bryan D. Stewart; Andrew C. Landsman

(57) ABSTRACT

A clavicle protective device may include a contoured member configured to cover at least a portion of the clavicle. The contoured member may have an inner surface configured to face the at least a portion of the clavicle and an outer surface configured to face away from the at least a portion of the clavicle. The contoured member may include a first contact portion, a second contact portion, and a bridge portion positioned between the first contact portion and the second contact portion. The first contact portion may be configured to contact the subject's body above the clavicle. The second contact portion may be configured to contact the subject's body below the clavicle. The bridge portion may be configured to be spaced apart from the subject's body when the first contact portion and the second contact portion contact the subject's body.

26 Claims, 21 Drawing Sheets

Related U.S. Application Data which is a continuation-in-part of application No. 29/748,100, filed on Aug. 27, 2020, now Pat. No. Des. 961,094, application No. 17/505,171, filed on Oct. 19, 2021 is a continuation-in-part of application No. 29/707,563, filed on Sep. 29, 2019, now Pat. No. Des. 936,847.

(60) Provisional application No. 62/907,719, filed on Sep. 29, 2019.

(51) Int. Cl.
| | |
|---|---|
| *A61F 5/10* | (2006.01) |
| *A61F 13/06* | (2006.01) |
| *A61F 13/14* | (2006.01) |
| *A63B 71/12* | (2006.01) |

(58) Field of Classification Search
CPC ...... A61F 5/05; A61F 5/04; A61F 5/01; A61F 5/00; A63B 71/12
See application file for complete search history.

(56) References Cited

U.S. PATENT DOCUMENTS

| | | | |
|---|---|---|---|
| D181,676 | S | 12/1957 | Ristenpart |
| D310,278 | S | 8/1990 | Quinlan |
| D382,052 | S | 8/1997 | Bayer |
| D417,543 | S | 12/1999 | Gable |
| 6,629,945 | B1 | 10/2003 | Stromgren |
| D485,020 | S | 1/2004 | Yake |
| D554,386 | S | 11/2007 | Nobles |
| D555,254 | S | 11/2007 | Buethorn |
| D569,044 | S | 5/2008 | Crye |
| D599,025 | S | 8/2009 | Mayhew |
| 8,272,073 | B2 | 9/2012 | Arensdorf |
| D705,938 | S | 5/2014 | Mcdonald |
| D724,746 | S | 3/2015 | Ruel |
| D815,214 | S | 4/2018 | Lacy |
| D840,047 | S | 2/2019 | Koo |
| D858,788 | S | 9/2019 | Giddings |
| D861,185 | S | 9/2019 | Pihlavamaki |
| D863,577 | S | 10/2019 | Chobuathong |
| D865,183 | S | 10/2019 | Otani |
| D868,279 | S | 11/2019 | Chiu |
| D876,640 | S | 2/2020 | King |
| D882,808 | S | 4/2020 | Miller |
| D885,589 | S | 5/2020 | Marcil |
| D904,638 | S | 12/2020 | Shiota |
| D908,905 | S | 1/2021 | Braden |
| D908,906 | S | 1/2021 | Braden |
| D908,910 | S | 1/2021 | Ampert |
| D909,672 | S | 2/2021 | Williams |
| 11,882,888 | B1 * | 1/2024 | Bulleit ............... A41D 13/0512 |
| 2014/0298681 | A1 | 10/2014 | Epstein |

OTHER PUBLICATIONS

NFL. NFL 2020 1st and Future Winner, Protect3d, using 3D scanning and printing to help improve injury recovery. Dec. 14, 2020. http://www.nfl.com/playerhealthandsafety/equipment-and-innovation/1st-and-future/nfl-2020-1st-and-future-winner-protect3d-using-3d-scanning-and-printing-to-help (Year: 2020).

IMPACT Deltoid PAd, Arthron IMPACT, Ithaca Sports, [Post date unknown], [site seen Nov. 22, 2021] Seen at URL: https://www.ithacasports.com/deltpad.html?cmp=googleproducts&kw=deltpad&gclid=EAlalQobChMlg7be796i9AIVxdzlCh0zaAS2EAQYBiABEgLqPP%E2%80%A6 (Year. 2021).

Magic Silicone Should Pads, BOOMBA, getboomba.com, [Post date unknown], [site seen Nov. 22, 2021] Seen at URL: http://www.getboomba.com/products/silicone-shoulder-pads?currency=USD&variant=39441729224880&utm_medium=cpc&utm_source=googles&utm%E2%80%A6 (Year: 2021).

IMPACT A/C Shoulder Pad—Right, Standard (Under 250lbs), IMPACT, Amazon, [Post date Aug. 25, 2010 [site seen Nov. 22, 2021] Seen at URL: http://www.amazon.com/Impact-Shoulder-Pad-Standard-250lbs/dp/B0040UVTVA/ref=asc_df_B0040UVTVA/ (Year: 2010).

* cited by examiner

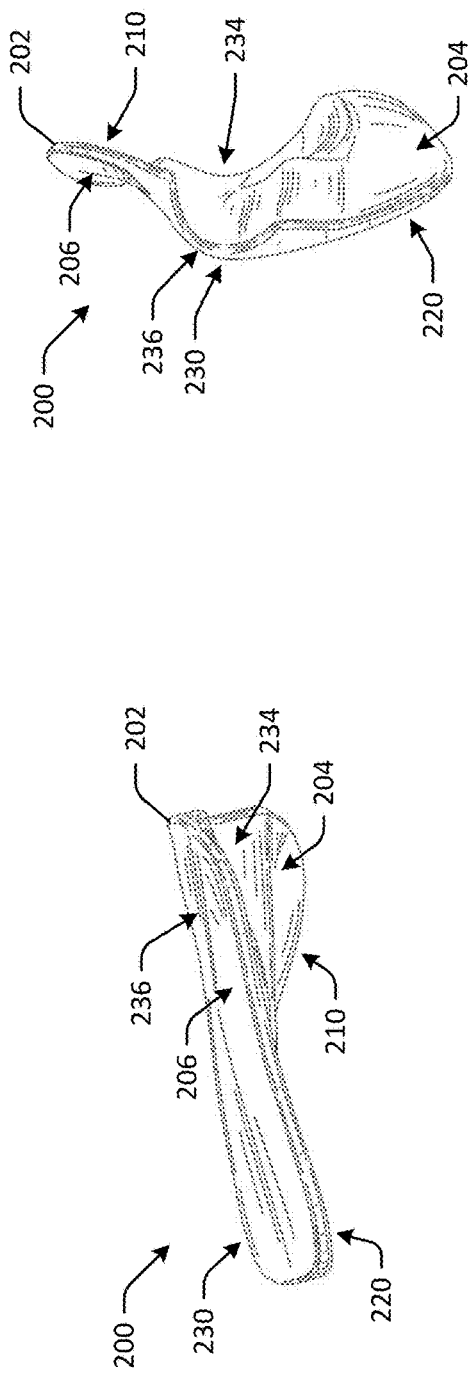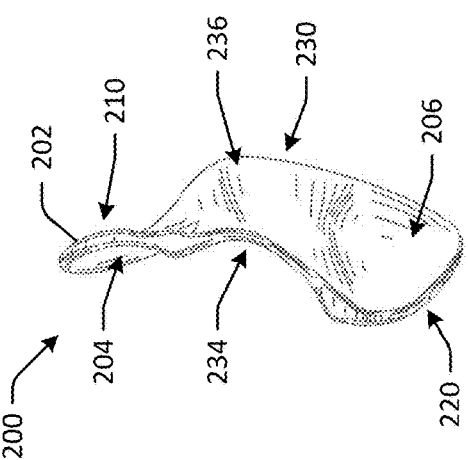
FIG. 2E
FIG. 2F
FIG. 2G

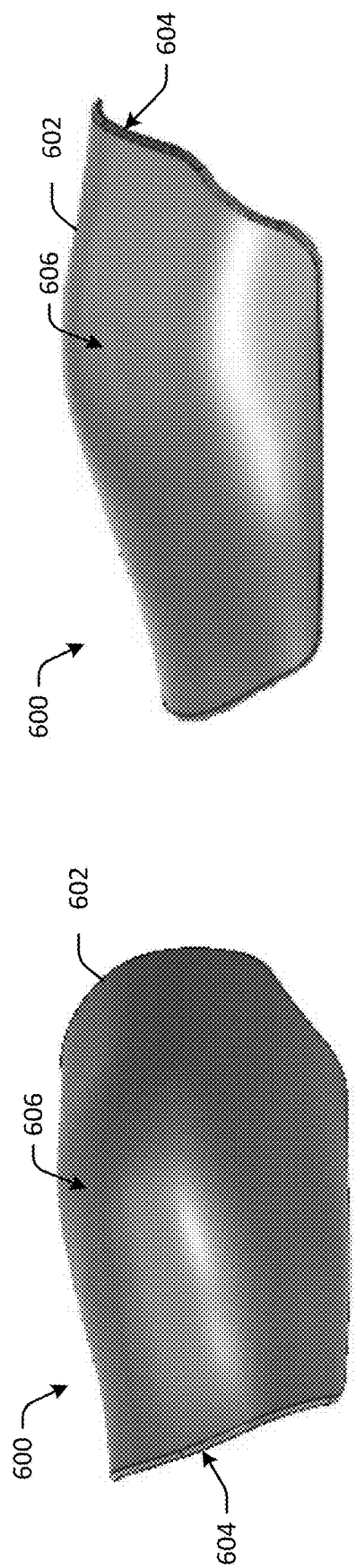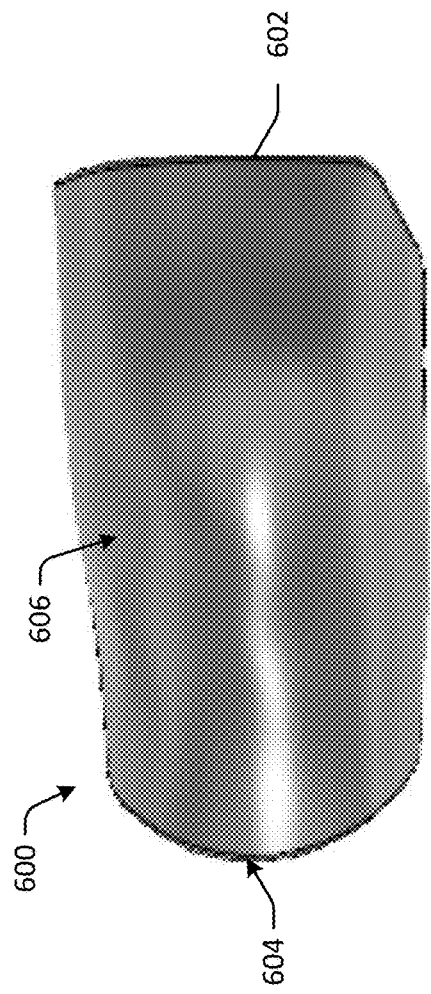
FIG. 6A  FIG. 6B  FIG. 6C

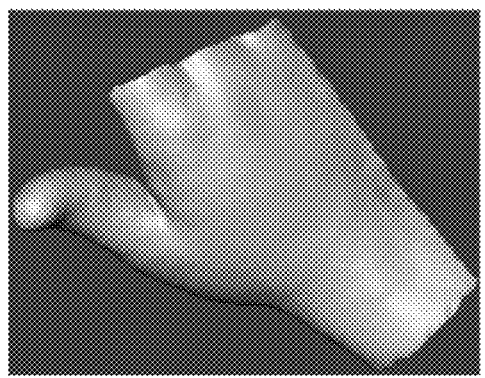
FIG. 13B
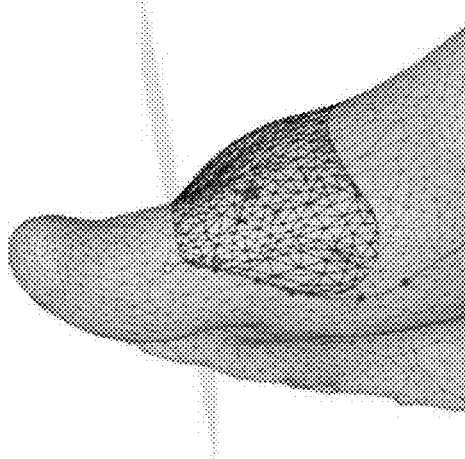
FIG. 13D
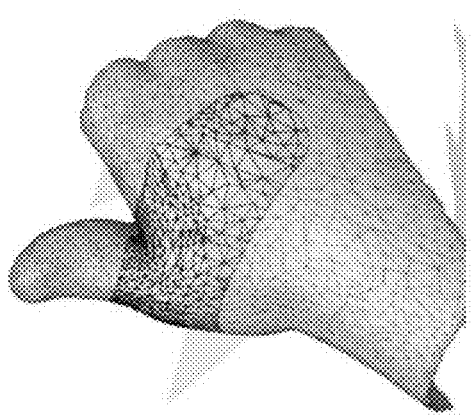
FIG. 13C
FIG. 13A

US 12,232,549 B1

CUSTOMIZED PROTECTIVE DEVICES AND SYSTEMS AND METHODS FOR PRODUCING THE SAME

CROSS REFERENCE TO RELATED APPLICATIONS

This application is a continuation-in-part of:

U.S. patent application Ser. No. 17/037,166, filed Sep. 29, 2020, entitled "CUSTOMIZED PROTECTIVE DEVICES AND SYSTEMS AND METHODS FOR PRODUCING THE SAME," which claims the benefit of and priority to U.S. Patent Application No. 62/907,719, filed Sep. 29, 2019, entitled "CUSTOMIZED PROTECTIVE DEVICES AND SYSTEMS AND METHODS FOR CREATING CUSTOMIZED PROTECTIVE DEVICES"; and is a continuation-in-part application of U.S. patent application Ser. No. 29/748,100, filed Aug. 27, 2020, entitled "AC JOINT PAD"; and U.S. patent application Ser. No. 29/707,563, filed Sep. 29, 2019, entitled "CLAVICLE BRACE";

each of the above are incorporated herein by reference in their entireties.

TECHNICAL FIELD

The present disclosure relates generally to protective devices wearable by a subject and more particularly to protective devices customized for wear by a particular subject to protect a portion of the subject's body from injury as well as related systems and methods for creating customized protective devices.

BACKGROUND

Protective devices often may be worn by a subject (i.e., a person) desiring to protect a particular portion of the subject's body, for example, during participation in athletic competition, military operations, or even daily activities. Example protective devices may include pads, braces, splints, supports, guards, shields, and other similar structural devices configured for covering or otherwise supporting a desired body portion. In some instances, protective devices may be used with respect to an uninjured body portion to prevent or inhibit injury thereof. In other instances, protective devices may be used with respect to an injured or previously injured body portion to prevent or inhibit further injury or re-injury of the body portion and promote desired healing. Providing protection for the intended body portion typically may be the primary goal in wearing a protective device, which may be achieved by constructing the device from suitable materials and to have a shape and size necessary to fit along and appropriately cover or support the intended body portion. However, additional goals often may include allowing the subject to maintain a normal range of motion while wearing the protective device and avoiding or minimizing any discomfort caused by wearing the device.

Various types of protective devices have been developed and used for different purposes in protecting particular body portions. Most commonly, standard off-the-shelf protective devices may be used by subjects seeking an affordable and readily-available device. Although standard protective devices may be available in different sizes or size ranges, such devices often may present certain limitations including, for example, improper fit, inadequate coverage, limited range of motion, and/or discomfort for a particular subject wearing the device. In some instances, a customized protective device may be created for a particular subject, thereby avoiding at least some of the limitations associated with standard devices. One technique for creating a customized protective device is hand molding of a thermoplastic substrate to cover an intended body portion, which is a practice widely used in collegiate and professional athletics. This technique, however, still may present certain shortcomings including, for example, constraints associated with the material, thickness, and geometry of the thermoplastic substrate as well as the experience and skill of the person molding the protective device. Thus, hand-molded protective devices may not be able to simultaneously achieve the desired goals of protection, mobility, and comfort. Another technique for creating a customized protective device involves casting a plaster mold around the intended body portion, and then forming the device based on a negative of the plaster mold in a process similar to injection molding. Although this technique may allow for greater variation in material, thickness, and geometry of the protective device as compared to hand-molded devices, the plaster-molding approach generally may be time-consuming and costly, particularly when multiple iterations are required to achieve a device that provides the protection, mobility, and comfort desired by the intended subject.

A need therefore exists for improved customized protective devices for protecting a portion of a subject's body from injury as well as related systems and methods for creating customized protective devices.

BRIEF SUMMARY OF THE DISCLOSURE

In various embodiments, the present disclosure provides customized protective devices for protecting a portion of a subject's body from injury as well as related systems and methods for creating customized protective devices. In one aspect, a clavicle protective device for protecting a clavicle of a subject is provided. In one embodiment, the clavicle protective device may include a contoured member configured to cover at least a portion of the clavicle. The contoured member may have an inner surface configured to face the at least a portion of the clavicle and an outer surface configured to face away from the at least a portion of the clavicle. In at least one embodiment, the inner surface substantially conforms to the at least a portion of the clavicle. The contoured member may include a first contact portion, a second contact portion, and a bridge portion positioned between the first contact portion and the second contact portion. The first contact portion may be configured to contact the subject's body above the clavicle. The second contact portion may be configured to contact the subject's body below the clavicle. The bridge portion may be configured to be spaced apart from the subject's body when the first contact portion and the second contact portion contact the subject's body.

In some embodiments, the first contact portion and the second contact portion may be spaced apart from one another by the bridge portion. In some embodiments, the bridge portion may be configured to extend over and be spaced apart from the at least a portion of the clavicle when the first contact portion and the second contact portion contact the subject's body. In some embodiments, the contoured member may have an outer profile surrounding each of the inner surface and the outer surface, and the bridge portion may extend from a first location at a first side of the outer profile to a second location at a second side of the outer profile. In some embodiments, the first side and the second side may be positioned opposite one another. In some embodiments, the bridge portion may have a length in a first direction extending from the first location to the second location and a width in a second direction transverse to the first direction, with the length being greater than the width.

In some embodiments, the bridge portion may include a channel extending along the inner surface. In some embodiments, the channel may have a curved profile along at least a portion of the bridge portion. In some embodiments, a curvature of the curved profile may vary along the at least a portion of the bridge portion. In some embodiments, the channel may have a U-shaped profile along at least a portion of the bridge portion. In some embodiments, the bridge portion may include a ridge extending along the outer surface. In some embodiments, the ridge may have a curved profile along at least a portion of the bridge portion. In some embodiments, the ridge may have a U-shaped profile along at least a portion of the bridge portion. In some embodiments, the contoured member may be formed of a material having an Izod impact strength that is equal to or greater than 90 J/m. In some embodiments, the material may have a flexural modulus that is equal to or greater than 0.7 GPa.

In another aspect, a method for creating a clavicle protective device for protecting a clavicle of a subject is provided. In one embodiment, a method for creating a clavicle protective device for protecting a clavicle of a subject may include: creating a digital three-dimensional surface model corresponding to at least a portion of a torso of the subject and a plurality of three-dimensional markers positioned on the at least a portion of the torso; creating a digital three-dimensional model of the clavicle protective device based at least in part on the digital three-dimensional surface model; and creating the clavicle protective device based at least in part on the digital three-dimensional model. The clavicle protective device may include a contoured member configured to cover at least a portion of the clavicle. The contoured member may include a first contact portion, a second contact portion, and a bridge portion positioned between the first contact portion and the second contact portion. The first contact portion may be configured to contact the subject's body above the clavicle. The second contact portion may be configured to contact the subject's body below the clavicle. The bridge portion may be configured to be spaced apart from the subject's body when the first contact portion and the second contact portion contact the subject's body.

In some embodiments, creating the digital three-dimensional surface model may include capturing a three-dimensional scan of the at least a portion of the torso and the plurality of three-dimensional markers. In some embodiments, the three-dimensional markers may be positioned along the clavicle. In some embodiments, the plurality of three-dimensional markers may include a first three-dimensional marker positioned over an acromioclavicular joint of the subject, a second three-dimensional marker positioned over a sternoclavicular joint of the subject; and a third three-dimensional marker positioned over the clavicle at an intermediate location between the acromioclavicular joint and the sternoclavicular joint. In some embodiments, creating the clavicle protective device may include creating the clavicle protective device by additive manufacturing.

In still another aspect, a method for creating a digital three-dimensional model of a clavicle protective device for protecting a clavicle of a subject is provided. In one embodiment, a method for creating a digital three-dimensional model of a clavicle protective device for protecting a clavicle of a subject may include: receiving a digital three-dimensional surface model corresponding to at least a portion of a torso of the subject and a plurality of three-dimensional markers positioned on the at least a portion of the torso; and creating a digital three-dimensional model of the clavicle protective device based at least in part on the digital three-dimensional surface model. The clavicle protective device may include a contoured member configured to cover at least a portion of the clavicle. The contoured member may include a first contact portion, a second contact portion, and a bridge portion positioned between the first contact portion and the second contact portion. The first contact portion may be configured to contact the subject's body above the clavicle. The second contact portion may be configured to contact the subject's body below the clavicle. The bridge portion may be configured to be spaced apart from the subject's body when the first contact portion and the second contact portion contact the subject's body.

In some embodiments, the three-dimensional markers may be positioned along the clavicle. In some embodiments, the plurality of three-dimensional markers may include a first three-dimensional marker positioned over an acromioclavicular joint of the subject, a second three-dimensional marker positioned over a sternoclavicular joint of the subject; and a third three-dimensional marker positioned over the clavicle at an intermediate location between the acromioclavicular joint and the sternoclavicular joint. In some embodiments, creating the digital three-dimensional model based at least in part on the digital three-dimensional surface model may include creating a first sketch line connecting a plurality of points corresponding to the plurality of three-dimensional markers. In some embodiments, a curvature of the bridge portion may correspond to a curvature of the first sketch line. In some embodiments, creating the digital three-dimensional model based at least in part on the digital three-dimensional surface model also may include: creating a second sketch line offset from the first sketch line and extending along the three-dimensional surface model; and creating a third sketch line offset from the first sketch line and extending along the three-dimensional surface model. In some embodiments, creating the digital three-dimensional model based at least in part on the digital three-dimensional surface model also may include creating a first non-uniform rational basis (NURB)-spline surface connecting the first sketch line, the second sketch line, and the third sketch line. In some embodiments, a shape of the bridge portion may correspond to a shape of the first NURB-spline surface. In some embodiments, creating the digital three-dimensional model based at least in part on the digital three-dimensional surface model also may include: creating a second NURB-spline surface extending from the first NURB-spline surface and along the three-dimensional surface model; and creating a third NURB-spline surface extending from the first NURB-spline surface and along the three-dimensional surface model. In some embodiments, a shape of the first contact portion may correspond to a shape of the second NURB-spline surface, and a shape of the second contact portion may correspond to a shape of the third NURB-spline surface.

In yet another aspect, a method for creating a digital three-dimensional model of a bone protective device for protecting a bone of a subject is provided. In one embodiment, a method for creating a digital three-dimensional model of a bone protective device for protecting a bone of a subject may include: receiving a digital three-dimensional surface model corresponding to at least a portion of a body of the subject and a plurality of three-dimensional markers positioned on the at least a portion of the body; and creating a digital three-dimensional model of the bone protective device based at least in part on the digital three-dimensional surface model. The bone protective device may include a contoured member configured to cover at least a portion of the bone. The contoured member may include a first contact portion, a second contact portion, and a bridge portion positioned between the first contact portion and the second contact portion. The first contact portion may be configured to contact the subject's body adjacent the bone. The second contact portion may be configured to contact the subject's body adjacent the bone. The bridge portion may be configured to be spaced apart from the subject's body when the first contact portion and the second contact portion contact the subject's body.

In some embodiments, the three-dimensional markers may be positioned along the bone. In some embodiments, the plurality of three-dimensional markers may include a first three-dimensional marker positioned over a first end of the bone, a second three-dimensional marker positioned over a second end of the bone; and a third three-dimensional marker positioned over the bone at an intermediate location between the first end and the second end. In some embodiments, creating the digital three-dimensional model based at least in part on the digital three-dimensional surface model may include creating a first sketch line connecting a plurality of points corresponding to the plurality of three-dimensional markers. In some embodiments, a curvature of the bridge portion may correspond to a curvature of the first sketch line. In some embodiments, creating the digital three-dimensional model based at least in part on the digital three-dimensional surface model also may include: creating a second sketch line offset from the first sketch line and extending along the three-dimensional surface model; and creating a third sketch line offset from the first sketch line and extending along the three-dimensional surface model. In some embodiments, creating the digital three-dimensional model based at least in part on the digital three-dimensional surface model also may include creating a first NURB-spline surface connecting the first sketch line, the second sketch line, and the third sketch line. In some embodiments, a shape of the bridge portion may correspond to a shape of the first NURB-spline surface. In some embodiments, creating the digital three-dimensional model based at least in part on the digital three-dimensional surface model also may include: creating a second NURB-spline surface extending from the first NURB-spline surface and along the three-dimensional surface model; and creating a third NURB-spline surface extending from the first NURB-spline surface and along the three-dimensional surface model. In some embodiments, a shape of the first contact portion may correspond to a shape of the second NURB-spline surface, and a shape of the second contact portion may correspond to a shape of the third NURB-spline surface.

According to a first aspect, a clavicle protective device for protecting a clavicle of a subject, the clavicle protective device including: A) a contoured member configured to cover at least a portion of a clavicle, wherein the contoured member includes: 1) an outer profile surrounding an inner surface and an outer surface, wherein the outer profile is defined at least in part from a boundary representation (BRep) solid modeling process performed on a point cloud of anatomical data collected from a subject's body; 2) the inner surface configured to face the portion of the clavicle and at least partially conforming to the anatomical data, wherein the inner surface is defined at least in part from a non-uniform rational basis (NURB)-spline surface modeling process performed on the point cloud of anatomical data collected from the subject's body; 3) the outer surface configured to face away from the portion of the clavicle; 4) a first contact portion configured to contact the subject's body above the clavicle; 5) a second contact portion configured to contact the subject's body below the clavicle; 6) a bridge portion positioned between the first contact portion and the second contact portion, wherein the bridge portion: a) is configured to be offset from the portion of the clavicle when the first contact portion and the second contact portion contact the subject's body; and b) extends from a first location at a first side of the outer profile to a second location at a second side of the outer profile; and c) includes a length in a first direction extending from the first location to the second location and a width in a second direction transverse to the first direction, and wherein the length is greater than the width; 7) an Izod impact strength of about 70 J/m; and 8) a flexural modulus of about 0.5 GPa.

According to a second aspect, the clavicle protective device of the first aspect or any other aspect, wherein the first contact portion and the second contact portion are spaced apart from one another by the bridge portion.

According to a third aspect, the clavicle protective device of the first aspect or any other aspect, wherein the bridge portion includes a channel extending along the inner surface.

According to a fourth aspect, the clavicle protective device of the third aspect or any other aspect, wherein at least a portion of the channel includes a curved profile.

According to a fifth aspect, the clavicle protective device of the fourth aspect or any other aspect, wherein a curvature of the curved profile varies along the at least a portion of the channel.

According to a sixth aspect, the clavicle protective device of the third aspect or any other aspect, wherein the channel includes a U-shaped profile.

According to a seventh aspect, the clavicle protective device of the sixth aspect or any other aspect, wherein the bridge portion further includes a ridge extending along the outer surface.

According to an eighth aspect, the clavicle protective device of the seventh aspect or any other aspect, wherein the ridge includes the curved profile.

According to a ninth aspect, the clavicle protective device of the seventh aspect or any other aspect, wherein the ridge includes the U-shaped profile.

According to a tenth aspect, the clavicle protective device of the first aspect or any other aspect, wherein the contoured member includes a thickness of about 4 mm.

According to an eleventh aspect, the clavicle protective device of the first aspect or any other aspect, wherein a magnitude of the offset is based at least in part on one or more peak points of the point cloud.

According to a twelfth aspect, a clavicle protective device for protecting a clavicle of a subject, the clavicle protective device including: A) a contoured member configured to cover at least a portion of a clavicle, wherein the contoured member includes: 1) an outer profile surrounding an inner surface and an outer surface, wherein the outer profile is defined at least in part from a boundary representation (BRep) solid modeling process performed on a point cloud of anatomical data collected from a subject's body; 2) the inner surface configured to face the portion of the clavicle and at least partially conforming to the anatomical data, wherein the inner surface is defined at least in part from a non-uniform rational basis (NURB)-spline surface modeling process performed on the point cloud of anatomical data collected from the subject's body; 3) the outer surface configured to face away from the portion of the clavicle; 4) a first contact portion configured to contact the subject's body above the clavicle; 5) a second contact portion configured to contact the subject's body below the clavicle; 6) a bridge portion positioned between the first contact portion and the second contact portion, wherein the bridge portion: a) is configured to be offset from the portion of the clavicle when the first contact portion and the second contact portion contact the subject's body, wherein a magnitude of the offset is based at least in part on one or more peak points of the point cloud; b) extends from a first location at a first side of the outer profile to a second location at a second side of the outer profile; and c) includes a length in a first direction extending from the first location to the second location and a width in a second direction transverse to the first direction, and wherein the length is greater than the width; 7) a thickness of about 4 mm; 8) an Izod impact strength of about 70 J/m; and 9) a flexural modulus of about 0.5 GPa.

According to a thirteenth aspect, the clavicle protective device of the twelfth aspect or any other aspect, wherein the first contact portion and the second contact portion are spaced apart from one another by the bridge portion.

According to a fourteenth aspect, the clavicle protective device of the twelfth aspect or any other aspect, wherein the bridge portion includes a channel extending along the inner surface.

According to a fifteenth aspect, the clavicle protective device of the fourteenth aspect or any other aspect, wherein at least a portion of the channel includes a curved profile.

According to a sixteenth aspect, the clavicle protective device of the fifteenth aspect or any other aspect, wherein a curvature of the curved profile varies along the at least a portion of the channel.

According to a seventeenth aspect, the clavicle protective device of the fourteenth aspect or any other aspect, wherein the channel includes a U-shaped profile.

According to an eighteenth aspect, the clavicle protective device of the seventeenth aspect or any other aspect, wherein the bridge portion further includes a ridge extending along the outer surface.

According to a nineteenth aspect, the clavicle protective device of the eighteenth aspect or any other aspect, wherein the ridge includes the curved profile.

According to a twentieth aspect, the clavicle protective device of the eighteenth aspect or any other aspect, wherein the ridge includes the U-shaped profile.

These and other aspects, features, and benefits of the claimed devices, systems, and methods will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 2E is a bottom view of the clavicle protective device of FIG. 2A;

FIG. 2F is a side view of the clavicle protective device of FIG. 2A;

FIG. 2G is a side view of the clavicle protective device of FIG. 2A;

FIG. 6A is a perspective view of an example finger joint protective device for protecting a finger joint of a subject in accordance with one or more embodiments of the disclosure;

FIG. 6B is a side view of the finger joint protective device of FIG. 6A;

FIG. 6C is a top view of the finger joint protective device of FIG. 6A;

FIG. 13A illustrates an example digital three-dimensional surface model created according to an example method for creating a customized thumb protective device for protecting a thumb of a subject in accordance with one or more embodiments of the disclosure, with the digital surface model corresponding to a portion of a hand of the subject, including the thumb;

FIG. 13B illustrates an example processed digital three-dimensional surface model created according to the example method, with the processed digital surface model corresponding to the portion of the subject's hand including the thumb;

FIG. 13C illustrates an example processed digital three-dimensional mesh model and a BRep body created according to the example method;

FIG. 13D illustrates the example processed digital three-dimensional mesh model and a processed BRep body created according to the example method;

DETAILED DESCRIPTION

Figure 1:
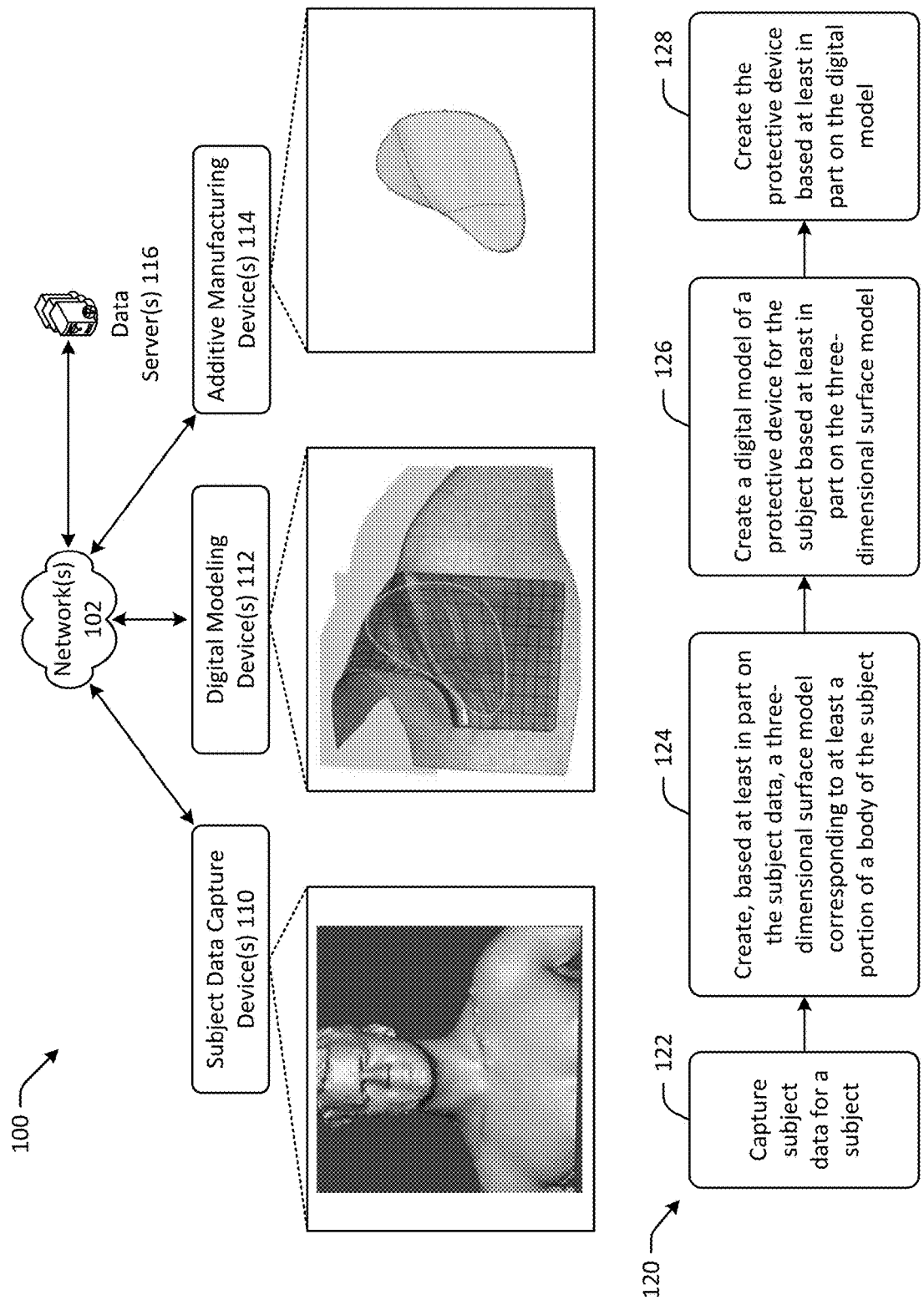
FIG. 1 illustrates an example architecture of a system for creating a customized protective device for protecting a body portion of a subject and an example method in accordance with one or more embodiments of the disclosure.
Figure 2A:
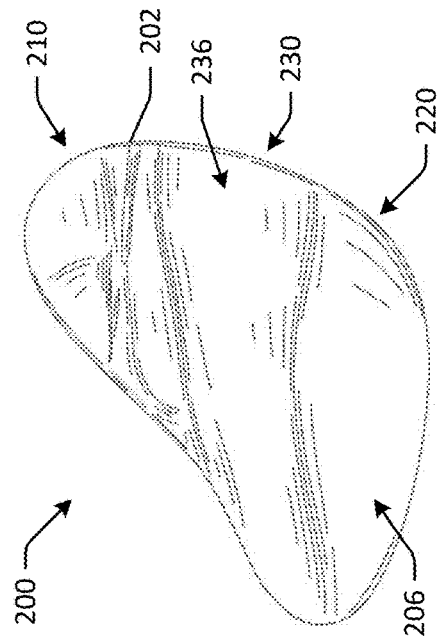
FIG. 2A is a perspective view of an example clavicle protective device for protecting a clavicle of a subject in accordance with one or more embodiments of the disclosure.
Figure 2B:
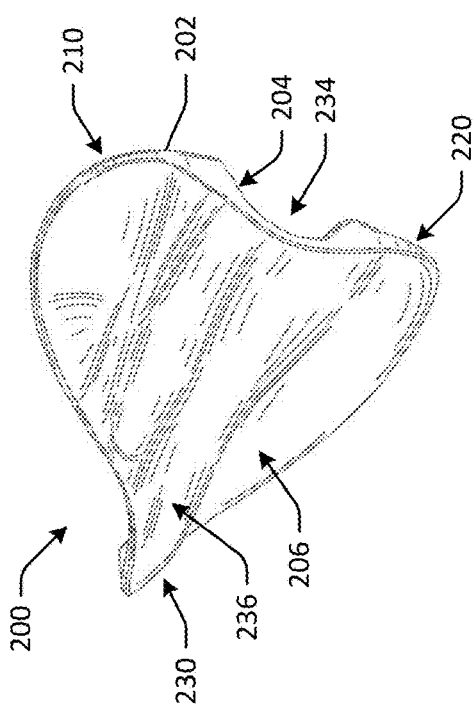
FIG. 2B is a front view of the clavicle protective device of FIG. 2A.
Figure 2C:
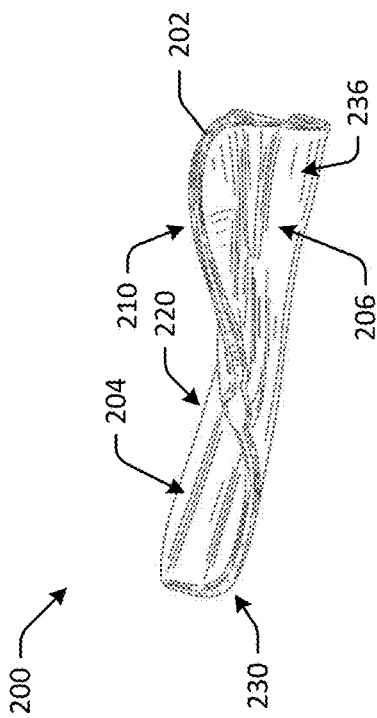
FIG. 2C is a rear view of the clavicle protective device of FIG. 2A.
Figure 2D:
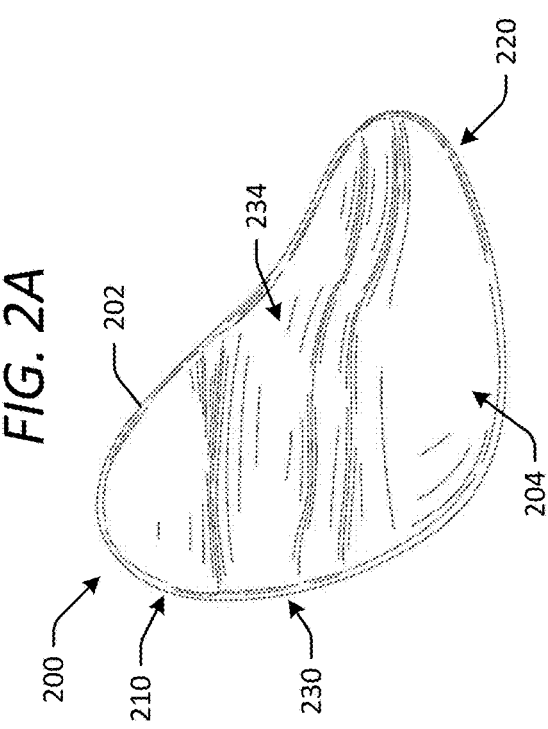
FIG. 2D is a top view of the clavicle protective device of FIG. 2A.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Embodiments of customized protective devices for protecting a portion of a body of a subject (i.e., a person) from injury as well as related systems and methods for creating customized protective devices are provided. As described herein, a customized protective device may be created for a particular subject in a manner that optimizes the goals of providing protection for the intended body portion, allowing the subject to maintain a normal range of motion, and avoiding or minimizing discomfort caused by wearing the device. The customized protective devices described herein generally may include a contoured member that is configured to cover (i.e., extend over) at least a portion of an intended body portion of the subject, with the contoured member having an inner surface and an outer surface disposed opposite one another. The inner surface may be configured to face the intended body portion when the customized protective device is worn by the subject, while the outer surface may be configured to face away from the intended body portion.

In some instances, a customized protective device may be configured for use with respect to an injured or previously injured body portion to prevent or inhibit further injury or re-injury of the body portion and promote desired hearing. In some embodiments, such a customized protective device may be configured to provide direct impact shielding for the injured or previously injured body portion. As described in detail below, direct impact shielding may be provided by configuring the customized protective device to include one or more contact portions and one or more non-contact portions. When the protective device is worn by the subject, the contact portion(s) may contact the subject's body, while the non-contact portion(s) may be offset (i.e., spaced apart) from the subject's body. In this manner, the non-contact portion(s) may cover an injured or previously injured body portion, while the contact portions distribute impact forces to surrounding body portions. In other embodiments, as described below, a customized protective device may be configured to limit a range of motion of a joint of the subject, for example, an injured joint, such that the joint is protected from further injury.

In some instances, a customized protective device may be configured for use with respect to an uninjured body portion to prevent or inhibit injury of the body portion. For example, such a customized protective device may be configured to cover a body portion that is likely to be impacted during participation in a given activity, such as contact sports. This type of customized protective device generally may be form-fit to the body portion to be protected, without any non-contact portions. Further, such a customized protective device may be configured to allow the subject to maintain a normal range of motion of nearby joints, while also avoiding undesired contact between the protective device and body portions other than those covered by the device.

Several types of customized protective devices are described herein and illustrated in the accompanying drawings. It will be appreciated that these protective devices are merely examples, and that features of the described and illustrated devices, as well as the methods for creating the devices, may be applied similarly to other types of customized protective devices for protecting other portions of a subject's body.

Referring now to FIG. 1, a system 100 for creating customized protective devices in accordance with one or more embodiments of the disclosure is depicted. The system 100 may be used for creating the example protective devices described herein as well as other devices. The system 100 generally may include one or more subject data capture device(s) 110, one or more digital modeling device(s) 112, and one or more additive manufacturing device(s) 114. The system 100 may include any number of these devices 110, 112, 114. In some embodiments, as shown, the subject data capture device 110, the digital modeling device 112, and the additive manufacturing device 114 may be in communication with one another via one or more network(s) 102. In this manner, the devices 110, 112, 114 may exchange data, such as subject data, digital models, or other types of data or information related to creation of customized protective devices, as described herein. In some embodiments, the devices 110, 112, 114 also may be in communication with one or more data server(s) 116, for example, via the network 102, to send data to the data server 116 for storage or to retrieve stored data from the data storage 116. Although the devices 110, 112, 114 and the data server 116 are depicted in FIG. 1 as separate devices, in some embodiments, two or more, or all, of these devices may be implemented as a single device.

The subject data capture device 110 may be configured to capture subject data for use in creating a customized protective device for a particular subject. In some embodiments, subject data includes, but is not limited to, anatomical data corresponding to spatial dimension and orientation of a subject's body (e.g., or a portion thereof, such as a forearm, torso, clavicle, hand, and etc.). In some embodiments, the subject data capture device 110 may be or may include a three-dimensional (3D) scanner, and the subject data may be a three-dimensional scan captured by the scanner. Various types of 3D scanners may be used, such as a structured-light scanner, a time-of-flight laser scanner, a triangulation-based laser scanner, or other suitable scanning device for obtaining a 3D scan. In some embodiments, the 3D scanner may have a capture rate that is equal to or greater than thirty (30) frames per second. Such a capture rate may be advantageous to avoid challenges in having the subject remain still long enough to capture a high-quality scan. In some embodiments, the 3D scanner may have a range that is equal to or greater than one (1) meter, which may be beneficial in view of a need to scan large anatomical features in a short time. In some embodiments, the 3D scanner may have an accuracy that is equal to or greater than five hundred (500) microns, providing the scanner with suitable precision to accurately represent all anatomical features in a digital manner. In some embodiments, the subject data capture device 110 may be or may include a photogrammetry device configured to capture and analyze photographic images.

The digital modeling device 112 may be configured to process subject data received from the subject data capture device 110 and create a digital model of a customized protective device for the intended subject. In doing so, the digital modeling device 112 may utilize various computer-aided design (CAD) software capabilities. In some embodiments, the subject data received from the subject data capture device 110 may be in the form of a point cloud (i.e., a set of data points arranged in three-dimensional space), and the digital modeling device 112 may transform the point cloud into a triangle mesh (i.e., a mesh of interlocking triangular surfaces), although other suitable types of polygon mesh may be used. The digital modeling device 112 then may manipulate the mesh into a form that is suitable for the creation of a customized protective device by processing and editing the mesh. For example, the digital modeling device 112 may perform various processing operations, such as cropping, cutting, merging, extruding, reducing, and filling. After processing the mesh, the digital modeling device 112 may digitally create the customized protective device. In other words, the digital modeling device 112 may create a digital model of the customized protective device. In creating the digital model of the customized protective device, the digital modeling device 112 may use one or more 3D modeling techniques.

In at least one embodiment, a technique includes non-uniform rational basis (NURB)-spline surface modeling, which may involve manipulating surfaces to create the customized protective device from the processed three-dimensional surface model for the intended subject. In various embodiments, a NURB-spline surface may be applied and mapped over the anatomical geometry of the three-dimensional surface model. In some embodiments, as described below, the NURB-spline surface may be manipulated to account for distribution of loads in view of the intended purpose of the protective device. The NURB-spline surface may be thickened to a thickness required for the specific protective device application, and then may be trimmed to a desired geometry for the application. This technique advantageously may allow for substantial design freedom to create complex hinges, bridge features, or other types of structural features. Use of the NURB-spline surface modeling technique is described further below with respect to certain example customized protective devices. In some embodiments, NURB-spline surface modeling includes generating and manipulating T-spline surfaces.

According to one embodiment, a second 3D modeling technique includes boundary representation (BRep) solid modeling, which may create a new solid body from the processed mesh. In one or more embodiments, the new body is different from the processed mesh, for example, because the boundaries of the solid body are represented mathematically within the software. In at least one embodiment, complex designs and patterns may be applied to create a desired shape of the customized protective device. The three-dimensional model for the subject may be brought into a computer program as a surface, converted and thickened into a body (BRep), and then trimmed down and altered in various ways to form a desired shape for the protective device. As discussed below, the BRep solid modeling technique may be useful in the creation of different types of customized protective devices.

The additive manufacturing device 114 may be configured to create a customized protective device using a digital model created by the digital modeling device 112. In some embodiments, the additive manufacturing device 114 may be or may include a 3D printer, such as a stereolithography (SLA) printer, although other suitable additive manufacturing techniques may be used. The properties of the material used to form the customized protective device generally may depend of the application and intended purpose of the device. As described below, certain types of protective devices may provide direct impact shielding form injured or previously injured body portions, for example, by creating the device with a bridge or dome structure. For such devices, the material used must highly impact resistant and stiff enough to resist deformation. In some embodiments, the material used for these devices may have an Izod impact strength that is equal to or greater than about 60-100 J/m, about 60-70 J/m, about 70 J/m, about 70-80 J/m, about 80-90 J/m, or about 90-100 J/m. In at least one embodiment, the material demonstrates a flexural modulus that is equal to or greater than about 0.4-0.9 GPa, about 0.4-0.5 GPa, about 0.5 GPa, about 0.5-0.6 GPa, about 0.6-0.7 GPa, about 0.7-0.8 GPa, or about 0.8-0.9 GPa. Other types of protective devices may be configured to prevent or inhibit rotation or movement of joints. For such applications, it may be advantageous to use a material that emphasizes stiffness over impact resistance. Additionally, the material may be sufficiently tough such that flexing is not likely to cause material failure. In some embodiments, the material for devices intended to prevent or inhibit rotation or movement of joints may have a flexural modulus that is equal to or greater than 0.85 GPa and an elongation at break of more than 50% in tensile testing. In various embodiments, the material of the protective devices is biocompatible and resists deformation during exposure to heat up to 150 degrees Fahrenheit. In some embodiments, a customized protective device may be formed of polypropylene photopolymer, although other suitable materials satisfying the necessary material properties may be used.

FIG. 1 depicts an example method 120 for creating a customized protective device for protecting a portion of a subject's body, as may be carried out using the system 100 described above. At step 122, the method 120 may include capturing subject data for a subject. For example, the subject data capture device 110 may be used to capture the subject data for the subject. In some embodiments, the subject data capture device 110 may be or may include a 3D scanner, which may capture the subject data in the form of a point cloud. The method 120 also may include, at step 124, creating a digital three-dimensional surface model corresponding to at least a portion of the subject's body. The digital three-dimensional surface model may be created based at least in part on the subject data. For example, the digital modeling device 112 may be used to receive the subject data from the subject data capture device 110 and create the digital three-dimensional surface model for the subject using the subject data. Various processing operations may be carried out in view of the intended protective device application. At step 126 of the method 120, a digital model of a protective device for the subject may be created based at least in part on the digital three-dimensional surface model. For example, the digital modeling device 112 may be used to create the digital model of the protective device based at least in part on the anatomical geometry of the digital three-dimensional surface model. Various modeling techniques may be used, as described above. At step 128, the method 120 may include creating the protective device based at least in part on the digital model. For example, the additive manufacturing device 114 may be used to create the protective device from the digital model using one or more additive manufacturing techniques. In some embodiments, the additive manufacturing device 114 may be or may include a 3D printer, which may form the protective device from a material suitable for the device's intended configuration and function. It will be appreciated that the method 120 sets forth the general steps for creating a customized protective device. Further details regarding particular example protective devices are provided below.

FIGS. 2A-2G illustrate an example clavicle protective device 200 for protecting a clavicle (i.e., a collarbone) of a subject in accordance with one or more embodiments of the disclosure. As shown, the clavicle protective device 200 may be in the form of a pad or brace configured to cover at least a portion of the subject's clavicle. The clavicle protective device 200 may be particularly useful for subjects engaging in contact sports after suffering a clavicle fracture, inhibiting re-injury and significant pain to the subject during the healing process. Existing methods for protecting the clavicle often restrict motion and are uncomfortable to wear. The clavicle protective device 200 not only addresses these issues but also functions to displace impact away from the healing clavicle.

As shown, the clavicle protective device 200 may include or be formed as a contoured member 202 that is configured to cover at least a portion of the intended subject's clavicle. The contoured member 202 may have an inner surface 204 configured to face the clavicle and an outer surface 206 configured to face away from the clavicle. The inner surface 204 can be configured to substantially, or at least partially, conform to anatomical data collected from the subject's body. In one example, the inner surface 204 is configured based on a point cloud of anatomical data that is collected from a scan of a subject's body. In this example, the inner surface 204 is configured to at least partially conform to the anatomical data such the inner surface 205 generally (or substantially) conforms to the subject's body. To provide impact displacement, the contoured member 202 may include one or more contact portions and one or more noncontact portions. In some embodiments, as shown, the contoured member 202 may include a first contact portion 210, a second contact portion 220, and a bridge portion 230. The contact portions 210, 220 may be configured to contact the subject's body adjacent to, and not on, the clavicle. In this manner, in the event that the clavicle protective device 200 is impacted, the contact portions 210, 220 may not transfer significant forces to the clavicle. As shown, the first contact portion 210 may be configured to contact the subject's body above the clavicle, and the second contact portion 220 may be configured to contact the subject's body below the clavicle. The bridge portion 230 may be positioned between the first contact portion 210 and the second contact portion 220 and configured to be spaced apart from the subject's body when the first contact portion 210 and the second contact portion 220 contact the subject's body. In other words, when the clavicle protective device 200 is properly positioned on the subject, a gap or spacing exists between the bridge portion 230 and the subject's body. In particular, according to the illustrated embodiment, the bridge portion 230 may be configured to extend over and be spaced apart from the portion of the clavicle covered by the contoured member 202 when the first contact portion 210 and the second contact portion 220 contact the subject's body. According to one embodiment, the bridge portion 230 is shaped to substantially conform to contours of a clavicle. In one example, a clavicle demonstrates a generally "S"-shaped cross-section and the bridge portion 230 is shaped to conform to the contours of the cross-section.

As shown, the first contact portion 210 and the second contact portion 220 may be spaced apart from one another by the bridge portion 230. In other words, in some embodiments, the first contact portion 210 and the second contact portion 220 do not contact one another. As shown, the contoured member 202 may have an outer profile (as viewed in FIGS. 2B and 2C) that surrounds each of the inner surface 204 and the outer surface 206. In some embodiments, as illustrated, the bridge portion 230 may extend from a first location at a first side of the outer profile to a second location at a second side of the outer profile, with the first side and the second side being positioned opposite one another. The bridge portion 230 may have a length in a first direction extending from the first location to the second location and a width in a second direction transverse to the first direction. In some embodiments, as shown, the length of the bridge portion 230 may be greater than the width of the bridge portion 230.

The bridge portion 230 may include a channel 234 extending along the inner surface 204 of the contoured member 202. As shown, the channel 234 may have a curved profile along at least a portion of the bridge portion 230. In some embodiments, a curvature of the curved profile of the channel 234 may vary along the at least a portion of the of the bridge portion 230. For example, the curvature of the curved profile of the channel 234 may correspond to the curvature of the subject's clavicle. In some embodiments, as shown, the channel 234 may have a U-shaped profile along at least a portion of the bridge portion 230. The bridge portion 230 may include a ridge 236 extending along the outer surface 206 of the contoured member 202. In some embodiments, the ridge 236 may have a curved profile along at least a portion of the bridge portion 230. In some embodiments, as shown, the ridge 236 may have a U-shaped profile along at least a portion of the bridge portion 230. The material used to form the contoured member 202 may be selected in accordance with the material properties discussed above (e.g., because the contoured member 202 may be configured to provide impact displacement). For example, the contoured member 202 may be formed of a material having an Izod impact strength that is equal to or greater than about 60-100 J/m, about 60-70 J/m, about 70 J/m, about 70-80 J/m, about 80-90 J/m, or about 90-100 J/m. In the same example, the material can demonstrate a flexural modulus that is equal to or greater than about 0.4-0.9 GPa, about 0.4-0.5 GPa, about 0.5 GPa, about 0.5-0.6 GPa, about 0.6-0.7 GPa, about 0.7-0.8 GPa, or about 0.8-0.9 GPa. In various embodiments, the combination of properties provides an advantageous combination of impact resistance and stiffness to enable desired function of the clavicle protective device 200, particularly for use in contact sports.

With reference to FIGS. 3A-3H, the following method may be used to create the clavicle protective device 200. The process may begin with positioning a plurality of markers on the subject. The markers may be three-dimensional or two-dimensional markers. In one or more embodiments, the markers are shaped or textured so as to be readily visible in a 3D scan of the subject's body when positioned thereon. Non-limiting examples of two-dimensional markers include, but are not limited to, adhesives, such as stickers, bodily drawings, and other two-dimensional indicia provided at a target site (e.g., a subject's body). For the purposes of illustration and discussion, the foregoing descriptions of device generation processes are placed in the context of three-dimensional markers; however, it will be understood by one of ordinary skill in the art that such processes may be performed using two-dimensional markers or a combination of two- and three-dimensional markers.

Figure 3B:
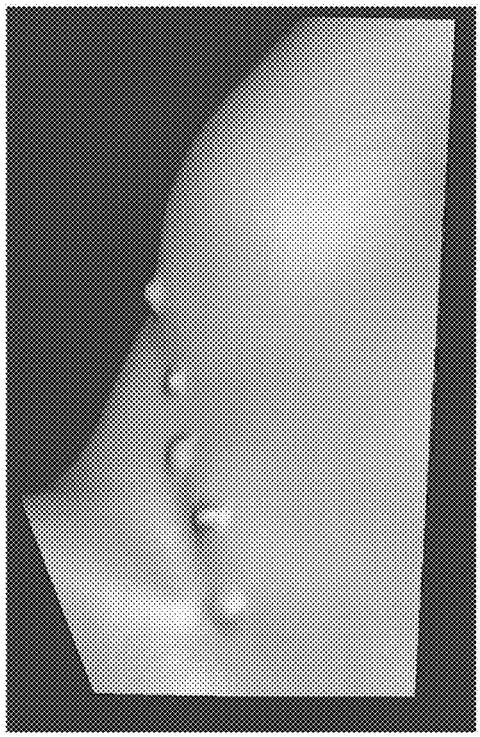
FIG. 3B illustrates an example processed digital three-dimensional surface model created according to the example method, with the processed digital surface model corresponding to a portion of the subject's body including the clavicle, at least a portion of the neck, and at least a portion of the shoulder.
Figure 3D:
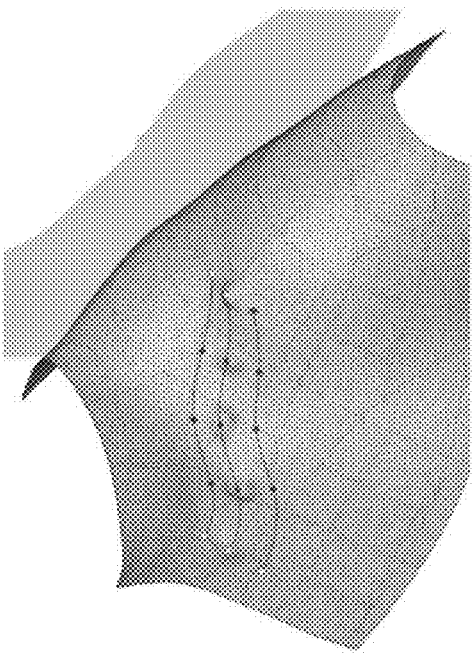
FIG. 3D illustrates the example processed digital three-dimensional surface model, the first sketch line, a second sketch line, and a third sketch line created according to the example method, showing the second sketch line and the third sketch line offset from the first sketch line and extending along the processed digital surface model.
Figure 3A:
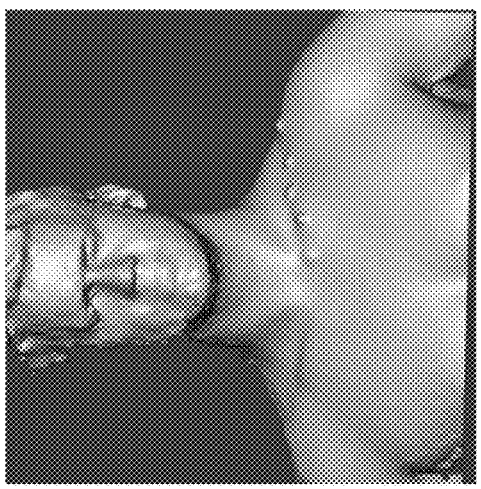
FIG. 3A illustrates an example digital three-dimensional surface model created according to an example method for creating a customized clavicle protective device for protecting a clavicle of a subject in accordance with one or more embodiments of the disclosure, with the digital surface model corresponding to a torso of the subject and a plurality of three-dimensional markers.

The markers may be positioned along the clavicle to allow the location and curvature of the clavicle to be readily determined from the 3D scan. In some embodiments, a first marker may be positioned over the acromioclavicular joint at the lateral end of the bone, and a second marker may be positioned over the sternoclavicular joint at the medial end of the bone. One or more additional markers may be positioned over the clavicle at one or more intermediate locations between the first and second markers to facilitate visualization of the curvature of the clavicle along its length in the 3D scan. A 3D scanner may be used to digitally capture a 3D surface model of at least a portion of the subject's torso. As discussed above, the 3D scanner may generate a point cloud (e.g., after positioning the markers on the subject's body). The point cloud may be converted into a raw standard tessellation language (.stl) file, as shown in FIG. 3A. In the depicted embodiment, five markers are visible, indicating the position and curvature of the clavicle. The .stl file may be imported into a mesh editing software for processing. FIG. 3B shows a cropped 3D surface model, including the relevant anatomy for properly creating the clavicle protective device 200. In at least one embodiment, one or more features to be included for modeling the clavicle protective device 200 include, but are not limited to, the clavicle, the adjacent curvature of the neck, and the entirety of the adjacent shoulder. During processing of the surface model, all stray surfaces may be deleted, and all holes may be filled to provide a continuous surface.

Figure 3C:
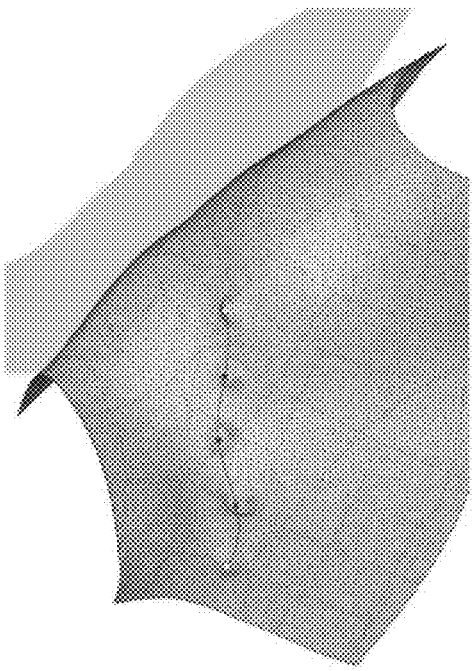
FIG. 3C illustrates the example processed digital three-dimensional surface model and a first sketch line created according to the example method, showing the first sketch line extending along points corresponding to the markers.

FIG. 3C shows the processed mesh as may be imported into software capable of NURB-spline surface modeling. In some embodiments, modeling of the clavicle protective device 200 includes creating a first sketch line that follows the curvature of the clavicle and connects a plurality of points corresponding to the plurality of markers. As shown in FIG. 3C, the sketch line may have a curved line having a curved 3D shape that follows the markers and thus the curvature of the clavicle. A second sketch line and a third sketch line may be created, as shown in FIG. 3D, with the second and third sketch lines each being offset from the first sketch line. The second sketch line may be offset above the first sketch line and may extend along the surface model, while the third sketch line may be offset below the first sketch line and may extend along the surface model. In this manner, the second and third sketch lines may be form-fit to the corresponding anatomy of the surface model, while the first sketch line may be fit to the peaks of the markers of the surface model, as shown. According to one embodiment, peak points of a point cloud (e.g., which may correspond to peaks of markers used in scanning a subject) at least partially define a magnitude by which a bridge portion is offset from a subject's body (e.g., when one or more contact portions of the protective device contact the subject's body). In some embodiments, the amount of offset of the second and third sketch lines from the first sketch line may be determined based on the thickness and anatomy of the subject's clavicle. The three sketch lines may be used to create the bridge portion 230 with an appropriate size and curvature for the subject's clavicle.

Figure 3F:
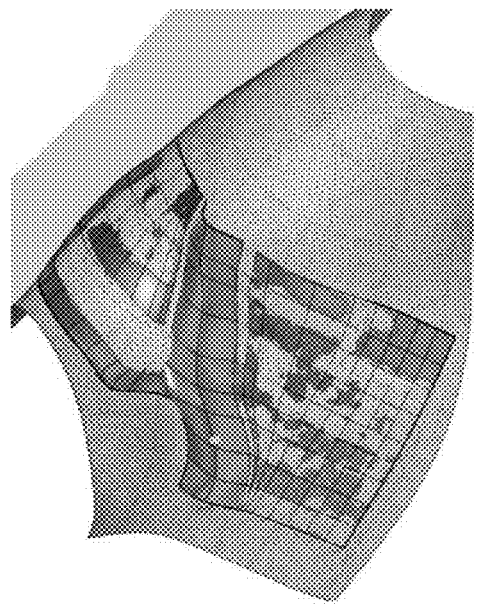
FIG. 3F illustrates the example processed digital three-dimensional surface model, the first NURB-spline surface, a second NURB-spline surface, and a third NURB-spline surface created according to the example method, showing the second NURB-spline surface and the third NURB-spline surface extending from the first NURB-spline surface and along the processed digital surface model.
Figure 3H:
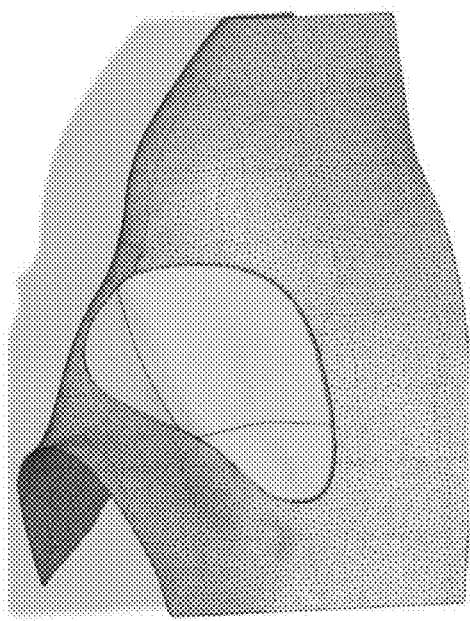
FIG. 3H illustrates the example processed digital three-dimensional surface model and a digital three-dimensional model of the customized clavicle protective device created according to the example method, showing the customized clavicle protective device positioned over an intended body portion of the subject.
Figure 3E:
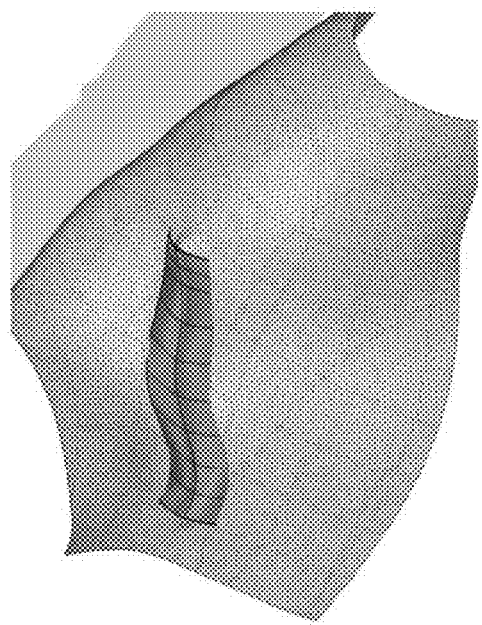
FIG. 3E illustrates the example processed digital three-dimensional surface model and a first non-uniform rational basis (NURB)-spline surface created according to the example method, showing the first NURB-spline surface connecting the first, second, and third sketch lines.
Figure 3G:
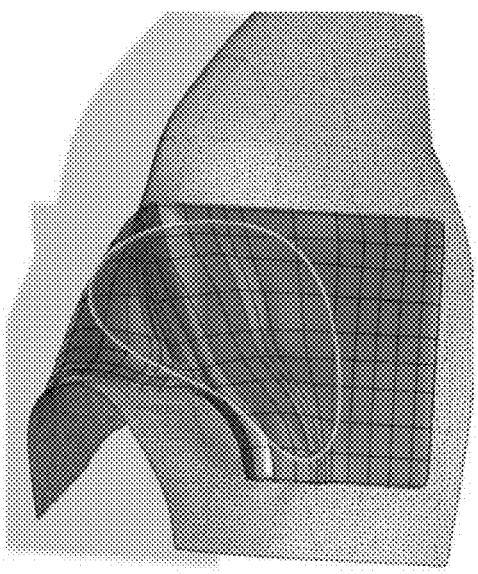
FIG. 3G illustrates the example processed digital three-dimensional surface model and the first, second, and third NURB-spline surfaces created according to the example method, showing the first, second, and third NURB-spline surfaces thickened and an outline corresponding to the customized clavicle protective device.
Figure 4B:
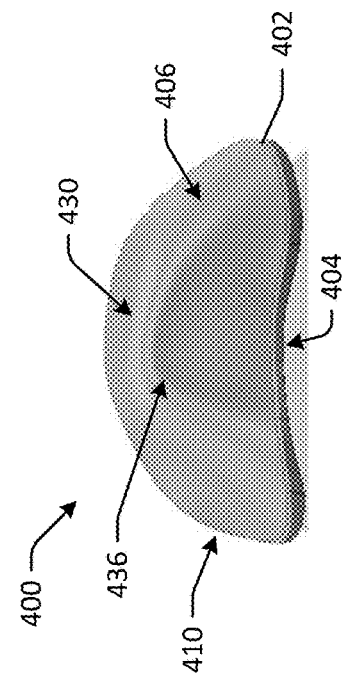
FIG. 4B is a top view of the acromioclavicular joint protective device of FIG. 4A.
Figure 4D:
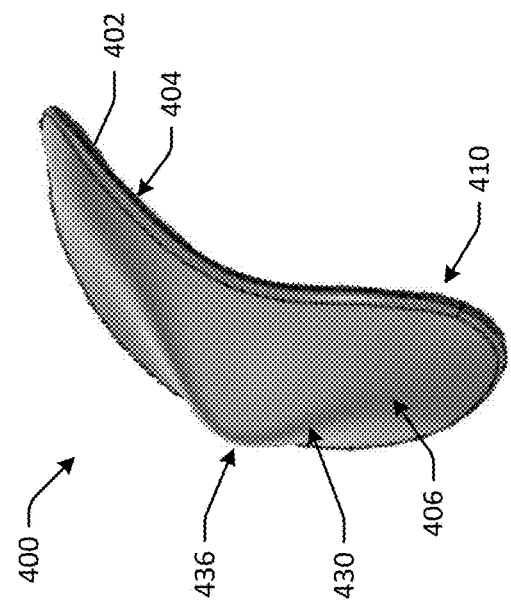
FIG. 4D is a side view of the acromioclavicular joint protective device of FIG. 4A.
Figure 4A:
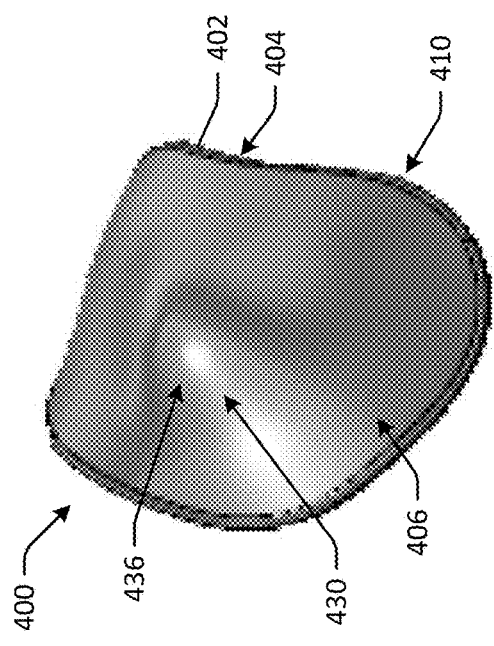
FIG. 4A is a front view of an example acromioclavicular joint protective device for protecting an acromioclavicular joint of a subject in accordance with one or more embodiments of the disclosure.
Figure 4C:
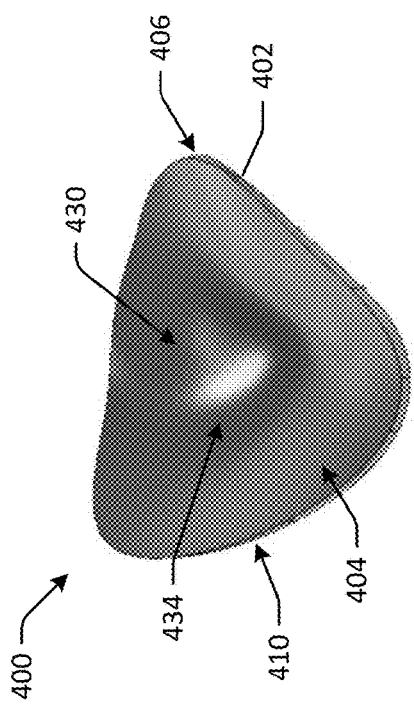
FIG. 4C is a bottom view of the acromioclavicular joint protective device of FIG. 4A.

After creation of the sketch lines, a first NURB-spline surface may be created, as illustrated in FIG. 3E. The height of the first NURB-spline surface may correspond to the heights of the markers, as shown. In this manner, the first NURB-spline surface may facilitate formation of the bridge portion 230. A second NURB-spline surface and a third NURB-spline surface then may be created, as shown in FIG. 3F, with the second NURB-spline surface extending upward from the first NURB-spline surface and along the anatomical surface geometry of the model, and the third NURB-spline surface extending downward from the first NURB-spline surface and along the anatomical surface geometry of the model. In this manner, the second NURB-spline surface and the third NURB-spline surface may be form-fit to the surface geometry of the model and thus the corresponding portions of the subject's body. Accordingly, the second and third NURB-spline surfaces may be used to create the first and second contact portions 210, 220 with an appropriate size and curvature for the subject's body. As shown in FIG. 3F, the entirety of the resulting overall NURB-spline surface (the combination of the first, second, and third NURB-spline surfaces) thus may be sized and shaped to contact the subject's body, except for the arched portion (corresponding to the bridge portion 230) that is raised up over the accurately mapped clavicle. The overall NURB-spline surface can be thickened, converted from a NURB-spline geometry into BRep, and cropped into the final shape of the intended clavicle protective device 200. In some embodiments, the 3D model of the clavicle protective device 200 may be thickened to about 1-8 mm, about 1-2 mm, about 2-3 mm, about 3-4 mm, about 4 mm, about 4-5 mm, about 5-6 mm, about 6-7 mm, or about 7-8 mm. The shape of the clavicle protective device 200 may be optimized to retain the greatest coverage of the clavicle while reducing contact points on the neck and shoulder.

FIGS. 4A-4D illustrate an example acromioclavicular joint protective device 400 for protecting an acromioclavicular (AC) joint of a subject in accordance with one or more embodiments of the disclosure. As shown, the AC protective device 400 may be in the form of a pad or brace configured to cover at least a portion of the subject's AC joint. In some embodiments, as shown, the AC protective device 400 is configured to cover the entire AC joint. The AC protective device 400 may be particularly useful for subjects engaging in contact sports after dislocation of the AC joint, inhibiting re-injury and significant pain to the subject during the healing process. Existing methods for protecting the AC joint often restrict motion, are uncomfortable to wear, and slip from the intended positioning during use. The AC protective device 400 not only addresses these issues but also functions to displace impact away from the healing AC joint.

As shown, the AC protective device 400 may include or be formed as a contoured member 402 that is configured to cover at least a portion of the intended subject's AC joint. The contoured member 402 may have an inner surface 404 configured to face the AC joint and an outer surface 406 configured to face away from the AC joint. To provide impact displacement, the contoured member 402 may include one or more contact portions and one or more noncontact portions. In some embodiments, as shown, the contoured member 402 may include a contact portion 410 and a dome portion 430. The contact portion 410 may be configured to contact the subject's body adjacent to, and not on, the AC joint. In this manner, in the event that the AC protective device 400 is impacted, the contact portion 410 will not transfer forces to the AC joint. As shown, the contact portion 410 may be configured to contact the subject's body surrounding the AC joint. The dome portion 430 may be surrounded by the contact portion 410 and configured to be spaced apart from the subject's body when the contact portion 410 contacts the subject's body. In other words, when the AC protective device 400 is properly positioned on the subject, a gap or spacing exists between the dome portion 430 and the subject's body. In particular, according to the illustrated embodiment, the dome portion 430 may be configured to extend over and be spaced apart from the portion of the AC joint covered by the contoured member 402 when the contact portion 410 contacts the subject's body.

As shown, the contact portion 410 may entirely surround the dome portion 430. In other words, in some embodiments, the contact portion 410 may extend entirely around the dome portion 430. The dome portion 430 may include an internal space 434 defined by the inner surface 404 of the contoured member 402. As shown, the internal space 434 may have a curved profile. For example, the curvature of the curved profile of the channel 434 may correspond to the curvature of the subject's AC joint. The dome portion 430 also may include a protrusion 436 defined by the outer surface 406 of the contoured member 402. In some embodiments, the protrusion 436 may have a curved profile. Material used to form the contoured member 402 may be selected in accordance with the material properties discussed above (e.g., because the contoured member 402 is configured to provide impact displacement). For example, the contoured member 402 may be formed of a material having an Izod impact strength that is equal to or greater than 90 J/m and a flexural modulus that is equal to or greater than 0.7 GPa. This combination of properties provides an advantageous combination of impact resistance and stiffness to enable desired function of the AC protective device 400, particularly for use in contact sports.

Figure 5A:
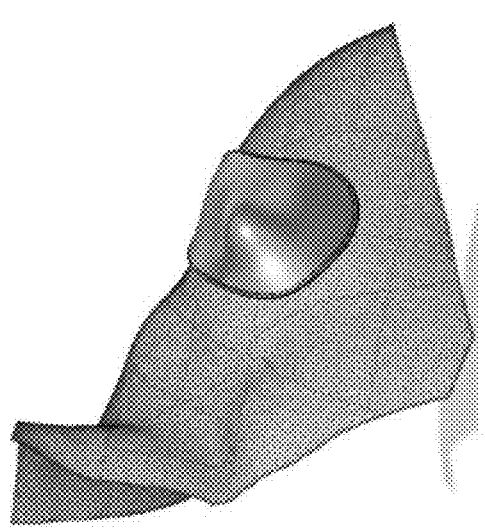
FIG. 5A illustrates an example processed digital three-dimensional surface model and NURB-spline surface created according to an example method for creating a customized acromioclavicular joint protective device for protecting an acromioclavicular joint of a subject in accordance with one or more embodiments of the disclosure, with the digital three-dimensional surface model corresponding to a portion of the subject's body including the acromioclavicular joint, at least a portion of the neck, and at least a portion of the shoulder.
Figure 5B:
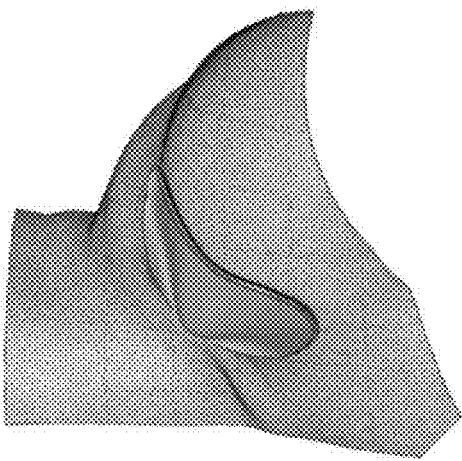
FIG. 5B illustrates the example processed digital three-dimensional surface model and a digital model of the customized acromioclavicular joint protective device created according to the example method, showing the customized acromioclavicular joint protective device positioned over an intended body portion of the subject.
Figure 5C:
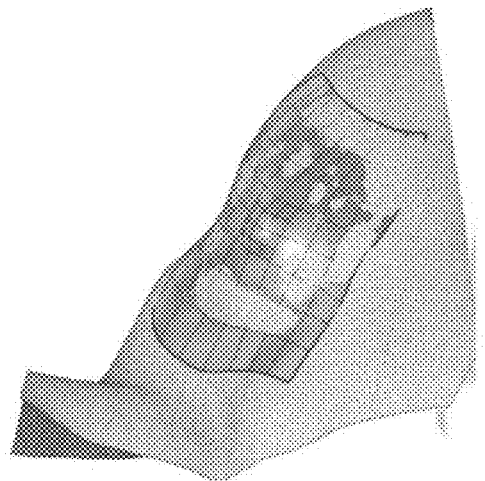
FIG. 5C illustrates the example processed digital three-dimensional surface model and the digital model of the customized acromioclavicular joint protective device created according to the example method.
Figure 5D:
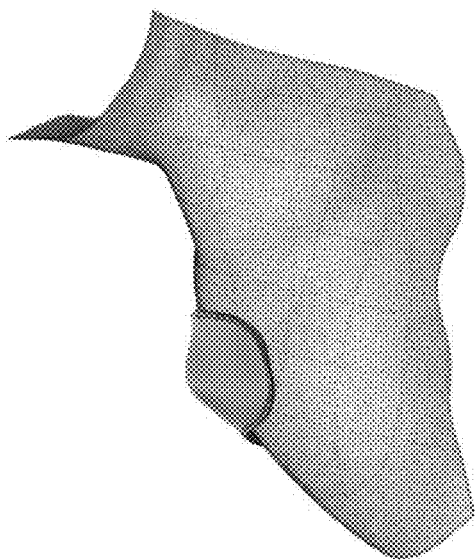
FIG. 5D illustrates the example processed digital three-dimensional surface model and the digital model of the customized acromioclavicular joint protective device created according to the example method.
Figure 7B:
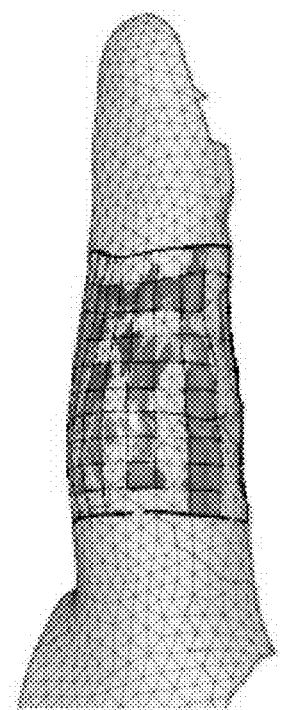
FIG. 7B illustrates an example processed digital three-dimensional surface model created according to the example method, with the processed digital three-dimensional surface model corresponding to a portion of the finger including the finger joint.
Figure 7D:
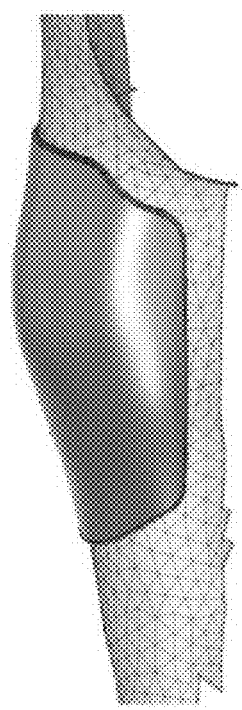
FIG. 7D illustrates the example processed digital three-dimensional surface model and the digital model of the customized finger joint protective device created according to the example method.
Figure 7A:
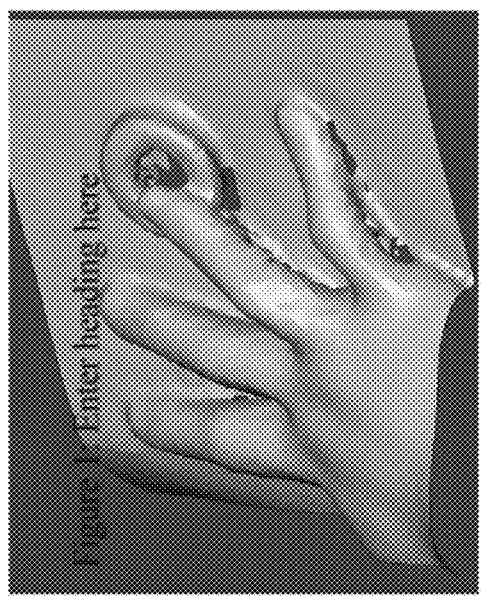
FIG. 7A illustrates an example digital three-dimensional surface model created according to an example method for creating a customized finger joint protective device for protecting a finger joint of a subject in accordance with one or more embodiments of the disclosure, with the digital three-dimensional surface model corresponding to a portion of a hand of the subject including a finger thereof.
Figure 7C:
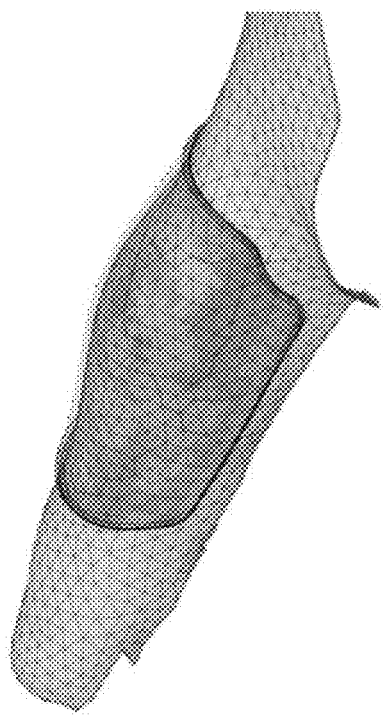
FIG. 7C illustrates the example processed digital three-dimensional surface model and a digital model of the customized finger joint protective device created according to the example method, showing the customized finger joint protective device positioned over an intended portion of the subject's finger.
Figure 8B:
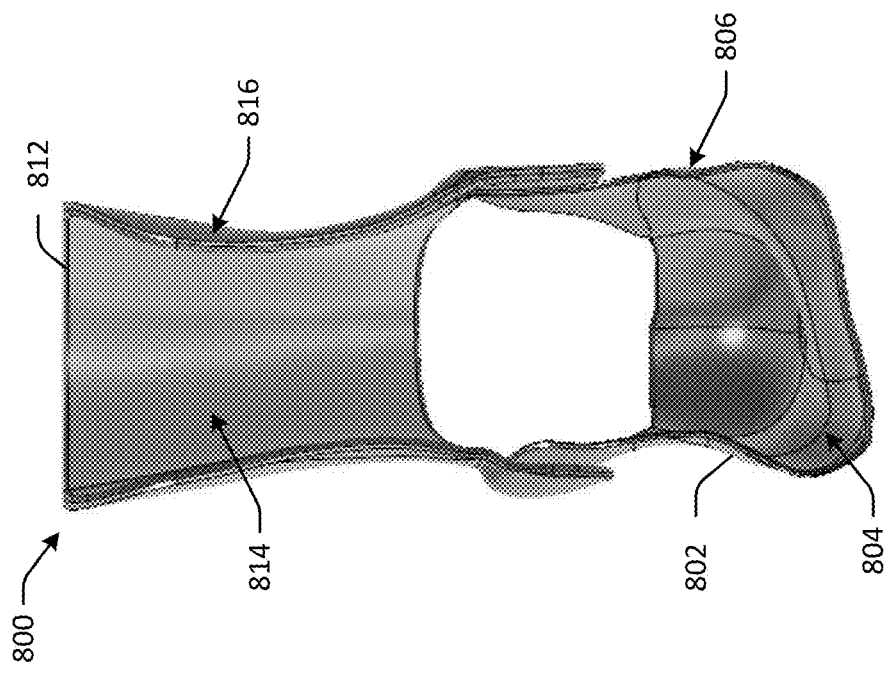
FIG. 8B is a front view of the ankle protective device of FIG. 8A.
Figure 8A:
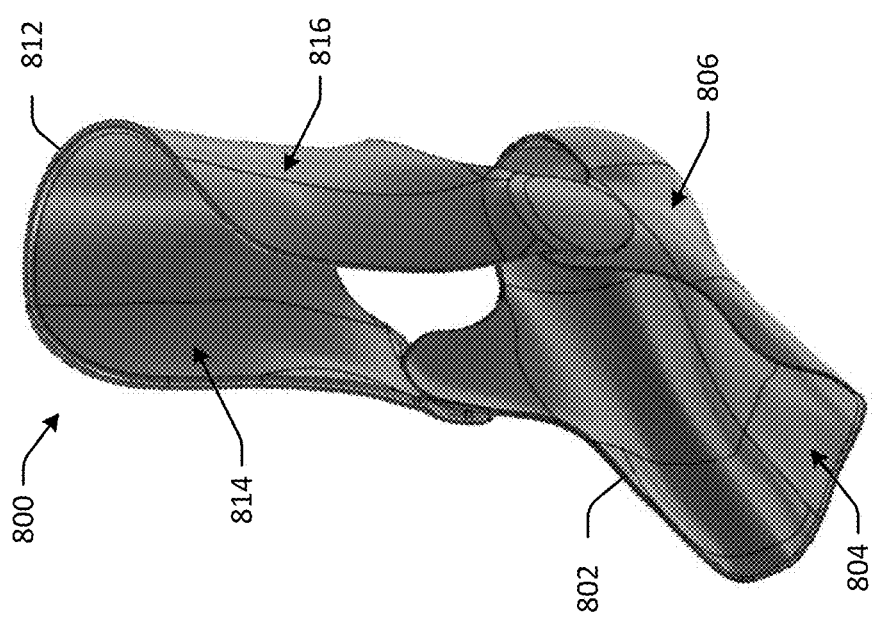
FIG. 8A is a perspective view of an example ankle protective device for protecting an ankle of a subject in accordance with one or more embodiments of the disclosure, with the ankle protective device including a first contoured member and a second contoured member coupled to one another by a pair of hinges.

With reference to FIGS. 5A-5H, the following method may be used to create the AC protective device 400. The process may begin with positioning a three-dimensional marker on the subject. The marker may be shaped or textured so as to be readily visible in a 3D scan of the subject's body when positioned thereon. The marker may be positioned over the subject's AC joint to allow the location and curvature of the AC joint to be readily determined from the 3D scan. A 3D scanner may be used (e.g., after positioning the marker on the subject's body) to digitally capture a 3D surface model of at least a portion of the subject's torso, including the AC joint and at least a portion of the subject's shoulder. As discussed above, the 3D scanner may generate a point cloud. The point cloud may be converted into a raw standard tessellation language (.stl) file. FIG. 5A shows a processed 3D surface model, including the relevant anatomy for properly creating the AC protective device 400. During processing of the surface model, all stray surfaces may be deleted, and all holes may be filled to provide a continuous surface. FIG. 5A shows the processed mesh as may be imported into software capable of NURB-spline surface modeling. The modeling of the AC protective device 400 may be carried out in a manner similar to that described above with respect to the clavicle protective device 200. As shown in FIG. 5A, a NURB-spline surface may be created. The NURB-spline surface may be thickened, converted from a NURB-spline geometry into BRep. and cropped into the final shape of the intended AC protective device 400, as shown in FIGS. 5B-5D. In some embodiments, the 3D model of the AC protective device 400 may be thickened to a particular magnitude, such as four (4) mm. The shape of the AC protective device 400 may be optimized to provide the greatest coverage of the AC joint while reducing contact points on the neck and shoulder that would restrict motion or cause discomfort.

FIGS. 6A-6D illustrate an example finger joint protective device 600 for protecting a joint of a finger of a subject, such as the proximal interphalangeal (PIP) joint, in accordance with one or more embodiments of the disclosure. As shown, the finger joint protective device 600 may be in the form of a pad or brace configured to cover at least a portion of the subject's finger joint. In some embodiments, as shown, the finger joint protective device 600 is configured to cover the entire finger joint. The finger joint protective device 600 may be particularly useful for subjects engaging in contact sports after dislocation of the finger joint, inhibiting re-injury and significant pain to the subject during the healing process. Alternatively, the finger joint protective device 600 may be used to prevent dislocation of the finger joint. As shown, the finger joint protective device 600 may include or be formed as a contoured member 602 that is configured to cover at least a portion of the intended subject's finger joint. The contoured member 602 may have an inner surface 604 configured to face the finger joint and an outer surface 606 configured to face away from the finger joint. The entirety of the inner surface 604 may be configured to contact the subject's finger and joint. In other words, the contoured member 602 may be configured such that the inner surface 604 form-fits to the subject's anatomy. FIGS. 7A-7D illustrate an example method for creating the finger joint protective device 600, which may be carried out in a manner as described above for the relevant anatomy.

Figure 9B:
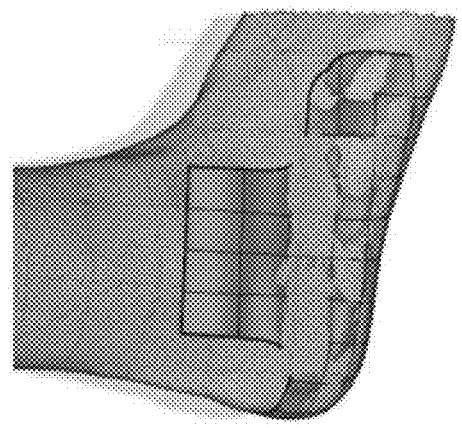
FIG. 9B illustrates an example processed digital three-dimensional surface model and a NURB-spline surface created according to the example method, with the processed digital three-dimensional surface model corresponding to the portion of the subject's body, with the NURB-spline surface corresponding to a first contoured member of the customized ankle protective device.
Figure 9D:
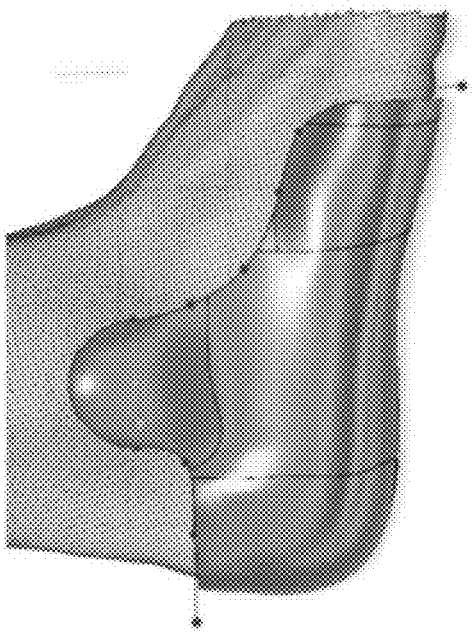
FIG. 9D illustrates the example processed digital three-dimensional surface model and a digital model of the first contoured member.
Figure 9A:
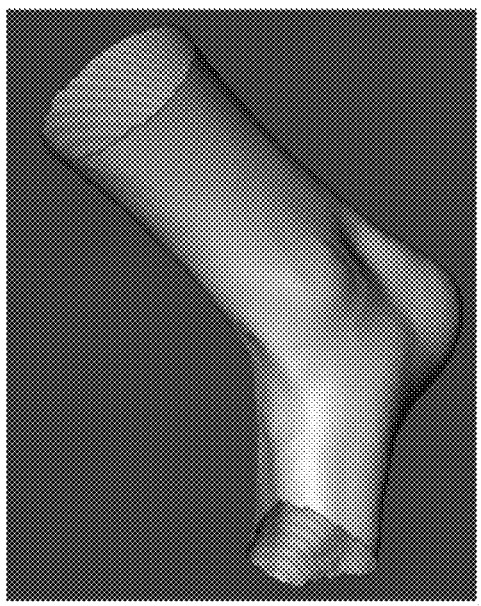
FIG. 9A illustrates an example digital three-dimensional surface model created according to an example method for creating a customized ankle protective device for protecting an ankle of a subject in accordance with one or more embodiments of the disclosure, with the digital three-dimensional surface model corresponding to a portion of the subject's body including the ankle, at least a portion of the foot, and at least a portion of the leg.
Figure 9C:
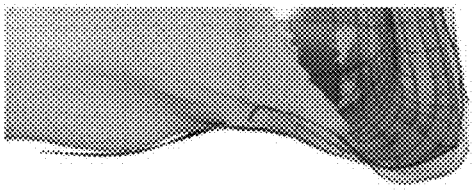
FIG. 9C illustrates the example processed digital three-dimensional surface model and a NURB-spline surface created according to the example method, with the NURB-spline surface corresponding to the first contoured member.
Figure 9F:
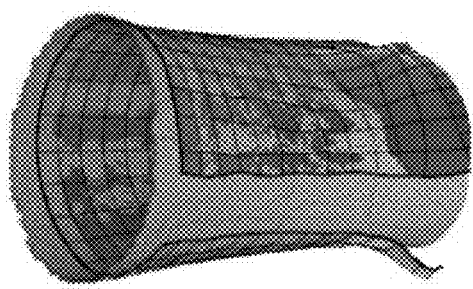
FIG. 9F illustrates the example processed digital three-dimensional surface model and a NURB-spline surface created according to the example method, with the NURB-spline surface corresponding to a second contoured member of the customized ankle protective device.
Figure 9H:
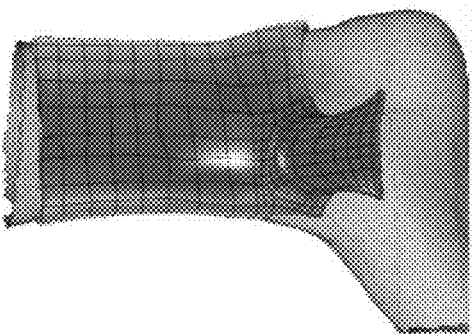
FIG. 9H illustrates the example processed digital three-dimensional surface model and a NURB-spline surface created according to the example method, with the NURB-spline surface corresponding to the second contoured member.
Figure 9E:
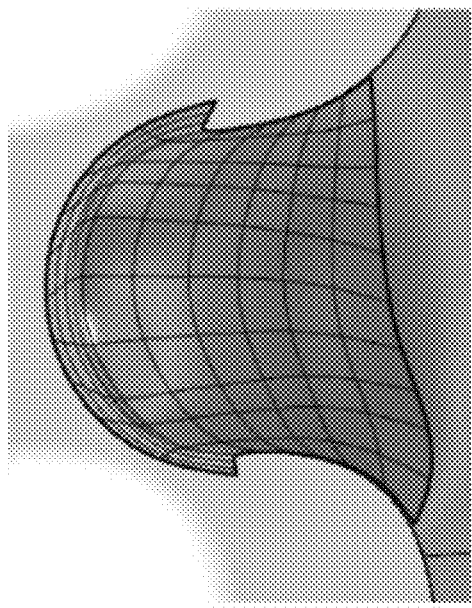
FIG. 9E illustrates a NURB-spline surface created according to the example method, with the NURB-spline surface corresponding to the first contoured member.
Figure 9G:
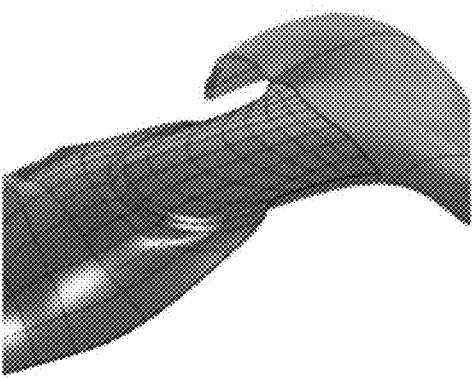
FIG. 9G illustrates the example processed digital three-dimensional surface model and a NURB-spline surface created according to the example method, with the NURB-spline surface corresponding to the second contoured member.
Figure 9J:
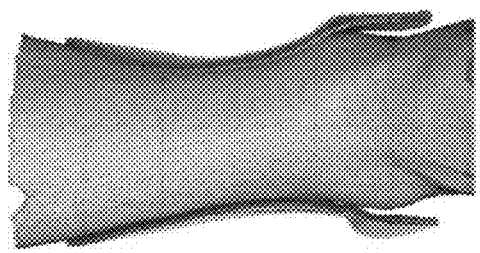
FIG. 9J illustrates the example processed digital three-dimensional surface model and the digital model of the second contoured member.
Figure 9L:
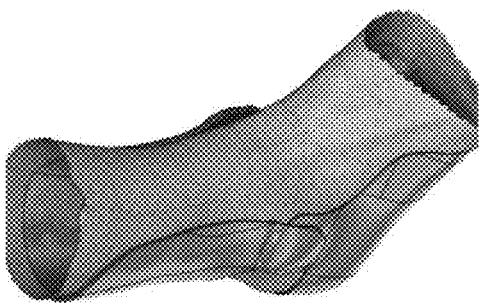
FIG. 9L illustrates the example processed digital three-dimensional surface model and the digital models of the first contoured member and the second contoured member.
Figure 9I:
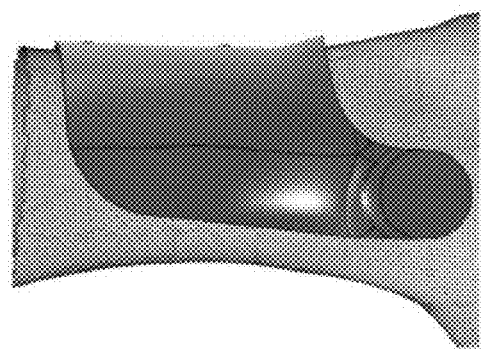
FIG. 9I illustrates the example processed digital three-dimensional surface model and a digital model of the second contoured member created according to the example method.
Figure 9K:
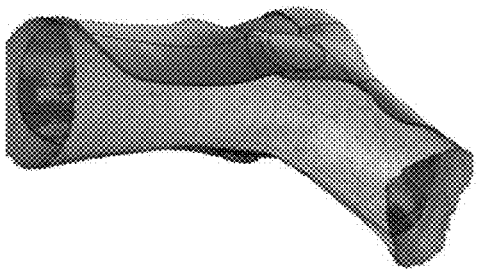
FIG. 9K illustrates the example processed digital three-dimensional surface model and the digital models of the first contoured member and the second contoured member.
Figure 9N:
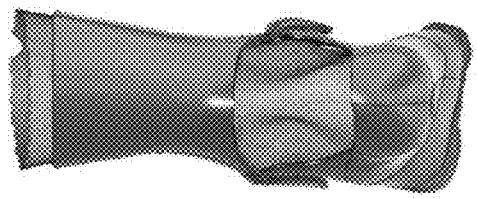
FIG. 9N illustrates the example processed digital three-dimensional surface model and the digital models of the first contoured member and the second contoured member.
Figure 9P:
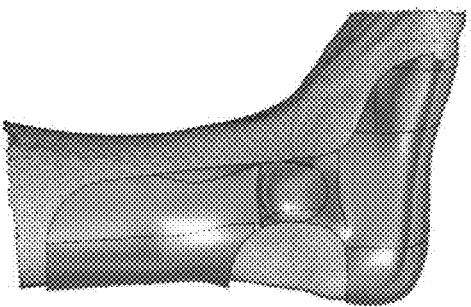
FIG. 9P illustrates the example processed digital three-dimensional surface model and the digital models of the first contoured member and the second contoured member.
Figure 9M:
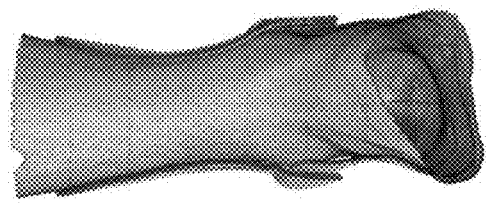
FIG. 9M illustrates the example processed digital three-dimensional surface model and the digital models of the first contoured member and the second contoured member.
Figure 9O:
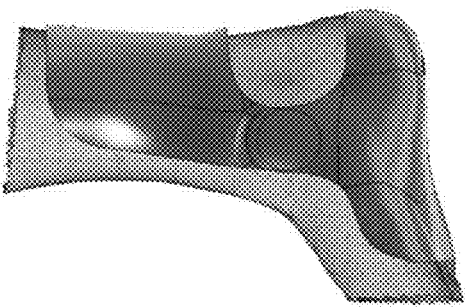
FIG. 9O illustrates the example processed digital three-dimensional surface model and the digital models of the first contoured member and the second contoured member.

FIGS. 8A-8D illustrate an example ankle protective device 800 for protecting an ankle of a subject in accordance with one or more embodiments of the disclosure. As shown, the ankle protective device 800 may be in the form of a brace configured to cover at least a portion of the subject's ankle. The ankle protective device 800 may be particularly useful for subjects engaging in contact sports after suffering a high ankle sprain, inhibiting re-injury and significant pain to the subject during the healing process by inhibiting rotation of the ankle. As shown, the ankle protective device 800 may include a first contoured member 802 configured to cover at least a portion of the intended subject's foot, and a second contoured member 812 configured to cover at least a portion of the intended subject's leg. The first contoured member 802 and the second contoured member 812 may be coupled to one another by a pair of hinges to allow restricted movement of the ankle. Each contoured member 802, 812 may have an inner surface 804, 814 configured to face the subject's anatomy and an outer surface 806, 816 configured to face away from the anatomy. Portions or all of the inner surfaces 804, 814 may be configured to contact the adjacent anatomy of the subject. In other words, portions or all of the contoured members 802, 812 may be configured such that the inner surfaces 804, 814 form-fit to the subject's anatomy. FIGS. 9A-9P illustrate an example method for creating the ankle protective device 800, which may be carried out in a manner as described above for the relevant anatomy.

Figure 10B:
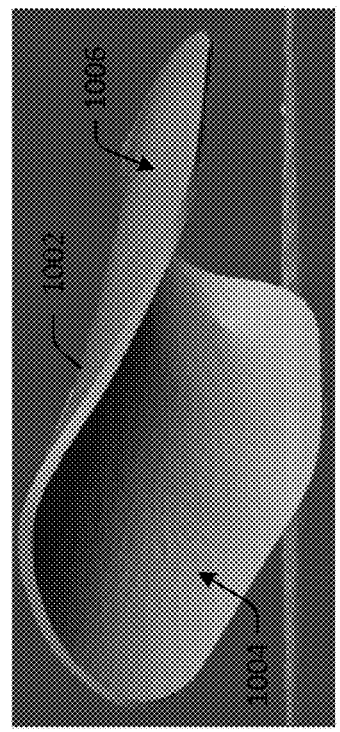
FIG. 10B is a perspective view of the forearm protective device of FIG. 10A.
Figure 10A:
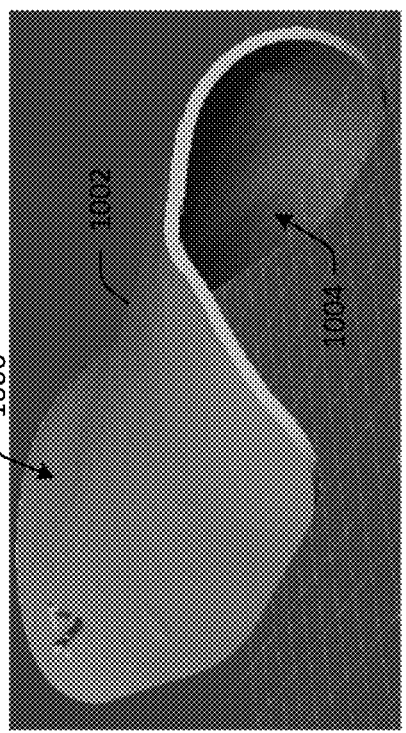
FIG. 10A is a perspective view of an example forearm protective device for protecting a forearm of a subject in accordance with one or more embodiments of the disclosure.
Figure 11A:
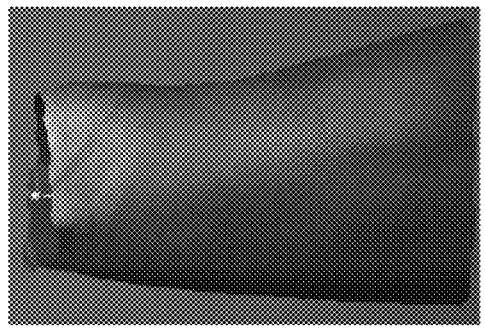
FIG. 11A illustrates an example digital three-dimensional surface model created according to an example method for creating a customized forearm protective device for protecting a forearm of a subject in accordance with one or more embodiments of the disclosure, with the digital surface model corresponding to a portion of an arm of the subject and a glove, including the forearm, and at least a portion of the bicep.
Figure 11B:
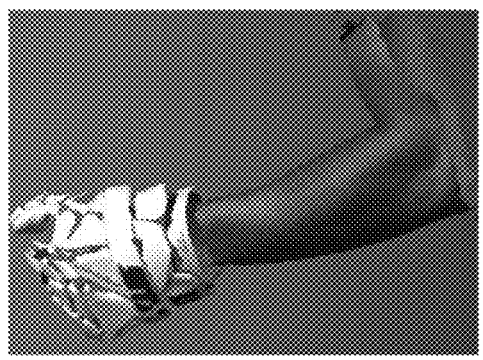
FIG. 11B illustrates an example processed digital three-dimensional surface model created according to the example method, with the processed digital surface model corresponding to a portion of the subject's arm including the forearm.
Figure 11C:
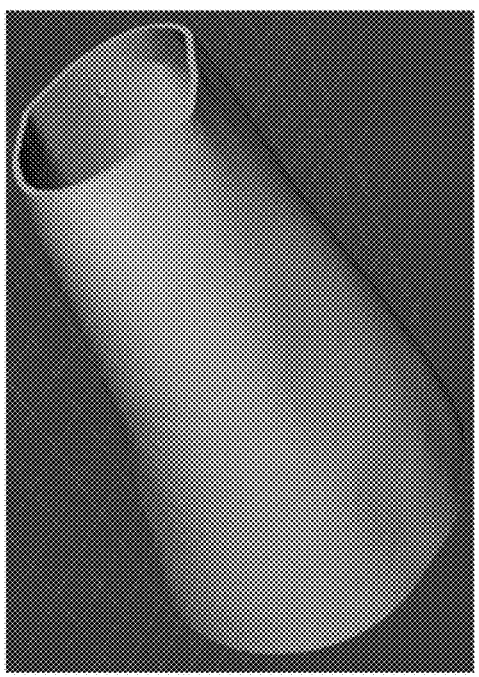
FIG. 11C illustrates a BRep body created using the processed digital three-dimensional surface model according to the example method.
Figure 11D:
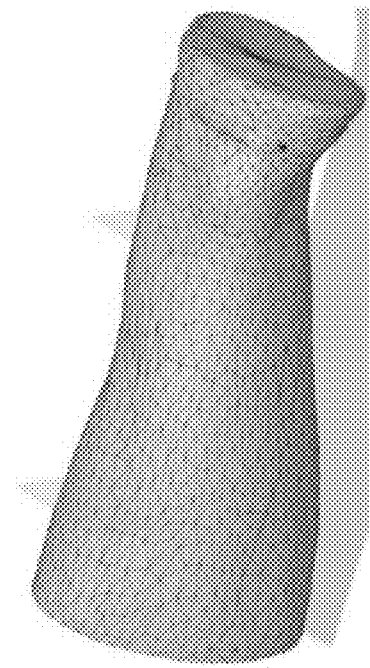
FIG. 11D illustrates a digital mesh model created according to the example method.
Figure 11F:
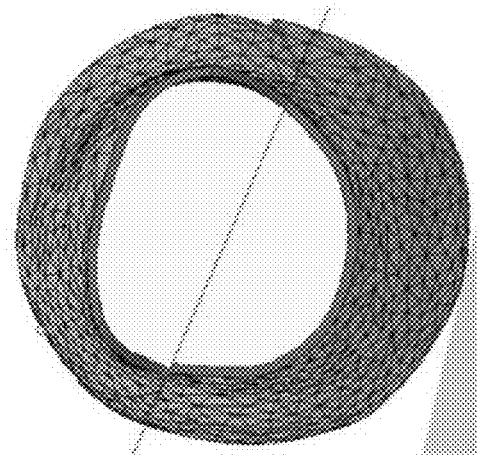
FIG. 11F illustrates a processed digital mesh model created according to the example method.
Figure 11G:
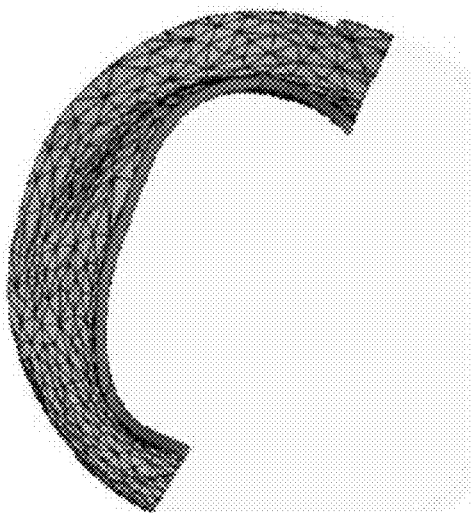
FIG. 11G illustrates a processed digital mesh model created according to the example method.
Figure 11E:
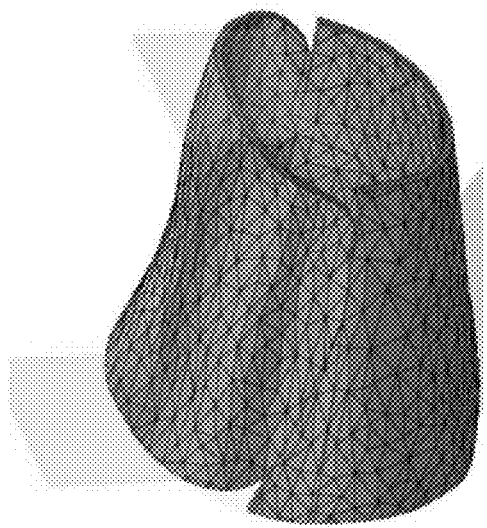
FIG. 11E illustrates a processed digital mesh model created according to the example method.
Figure 11I:
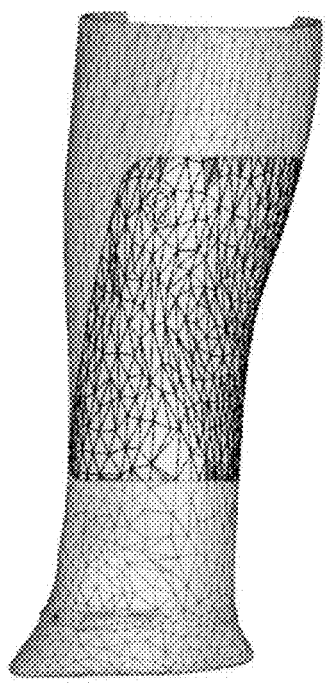
FIG. 11I illustrates the digital mesh model and the digital model of the forearm protective device.
Figure 11K:
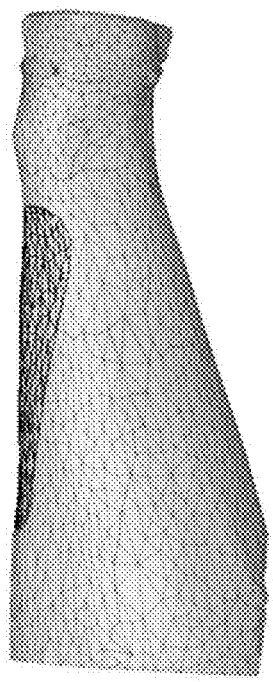
FIG. 11K illustrates the digital mesh model and the digital model of the forearm protective device.
Figure 11H:
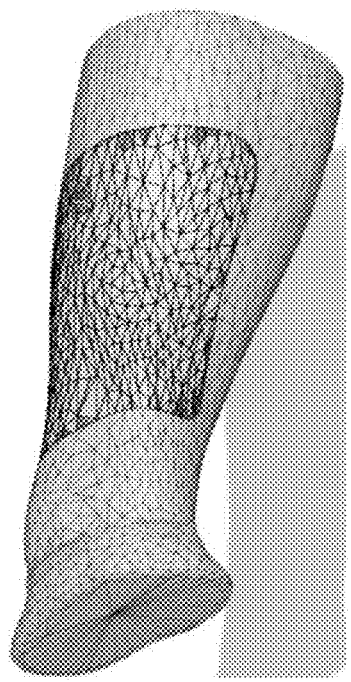
FIG. 11H illustrates the digital mesh model and a digital model of the forearm protective device created according to the example method.
Figure 11J:
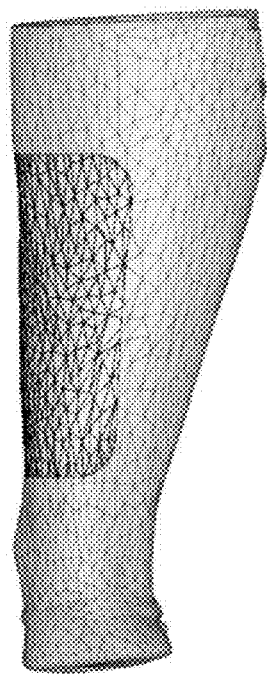
FIG. 11J illustrates the digital mesh model and the digital model of the forearm protective device.

FIGS. 10A-10B illustrate an example forearm protective device 1000 for protecting a forearm of a subject in accordance with one or more embodiments of the disclosure. As shown, the forearm protective device 1000 may be in the form of a pad or brace configured to cover at least a portion of the subject's forearm. In some embodiments, as shown, the forearm protective device 1000 is configured to cover a majority of the forearm. The forearm protective device 1000 may be particularly useful for subjects engaging in contact sports in which the forearm is often contacted, such as in lacrosse or hockey. As shown, the forearm protective device 1000 may include or be formed as a contoured member 1002 that is configured to cover at least a portion of the intended subject's forearm. The contoured member 1002 may have an inner surface 1004 configured to face the forearm and an outer surface 1006 configured to face away from the forearm. The entirety of the inner surface 1004 may be configured to contact the subject's forearm. In other words, the contoured member 1002 may be configured such that the inner surface 1004 form-fits to the subject's anatomy. FIGS. 11A-11K illustrate an example method for creating the forearm protective device 1000, which may be carried out in a manner as described above for the relevant anatomy.

Figure 12A:
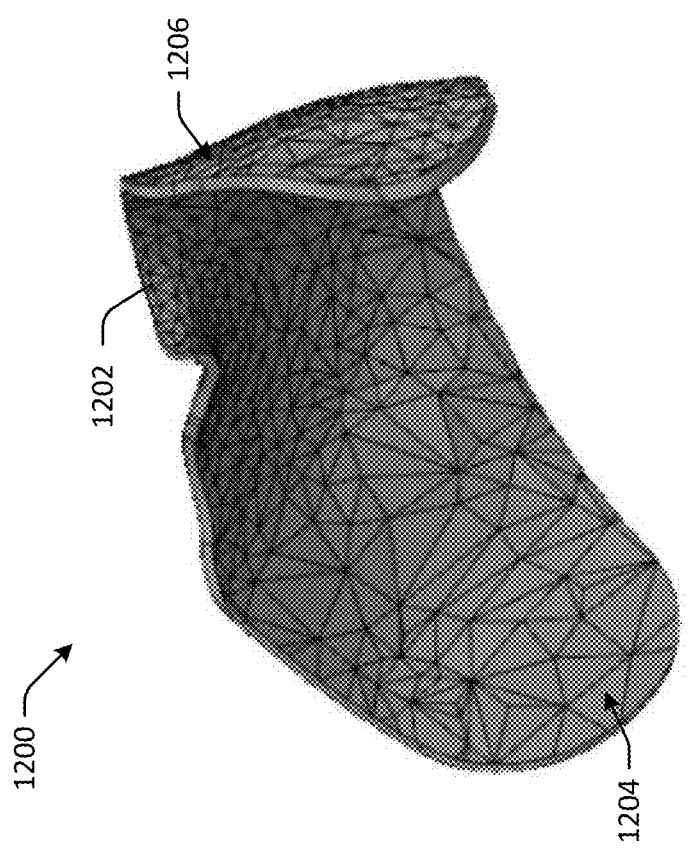
FIG. 12A is a perspective view of an example thumb protective device for protecting a thumb of a subject in accordance with one or more embodiments of the disclosure.
Figure 12B:
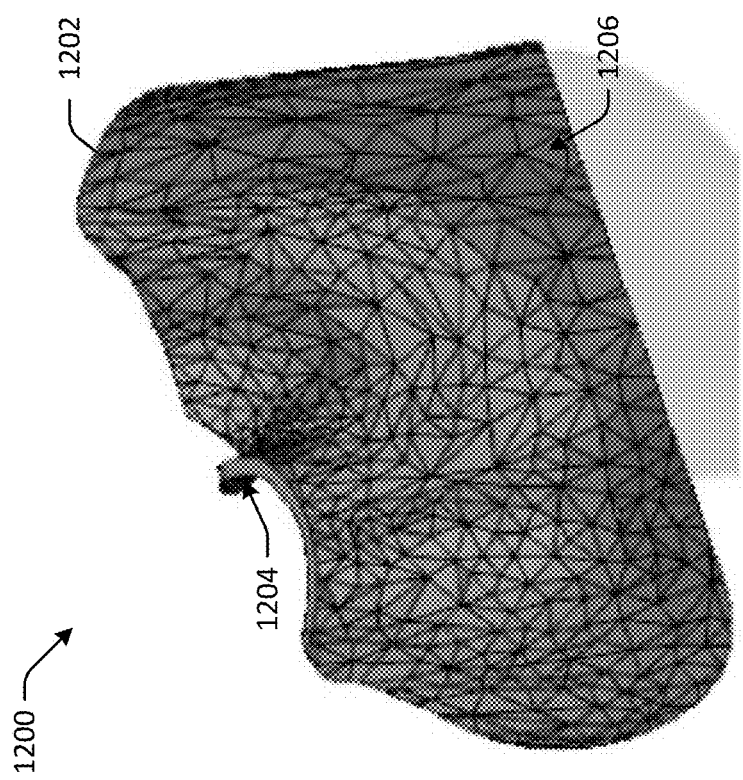
FIG. 12B is a perspective view of the thumb protective device of FIG. 12A.
Figure 13F:
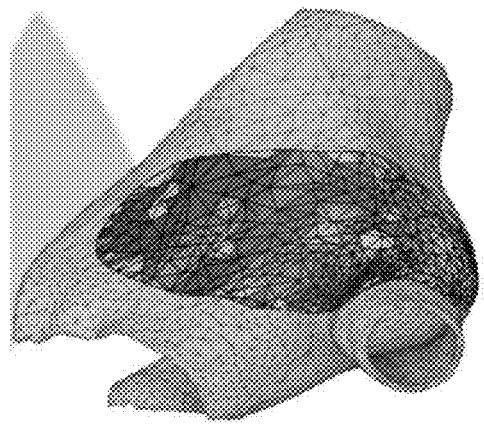
FIG. 13F illustrates the digital mesh model and the digital model of the thumb protective device.
Figure 13H:
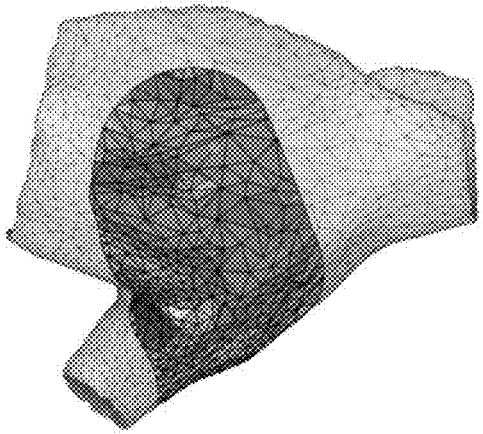
FIG. 13H illustrates the digital mesh model and the digital model of the thumb protective device.
Figure 13E:
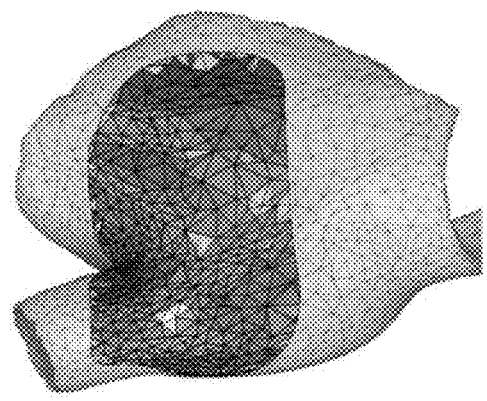
FIG. 13E illustrates the digital mesh model and a digital model of the thumb protective device created according to the example method.
Figure 13G:
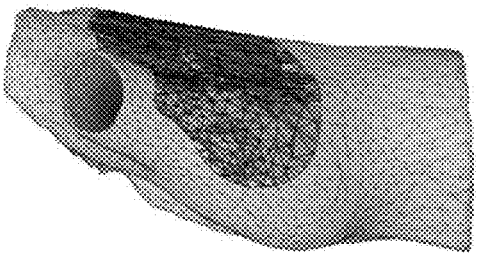
FIG. 13G illustrates the digital mesh model and the digital model of the thumb protective device.

FIGS. 12A-12B illustrate an example thumb protective device 1200 for protecting a thumb of a subject in accordance with one or more embodiments of the disclosure. As shown, the thumb protective device 1200 may be in the form of a pad or brace or support configured to cover at least a portion of the subject's thumb and hand. In some embodiments, as shown, the thumb protective device 1200 is configured to cover a majority of the thumb. The thumb protective device 1200 may be particularly useful for subjects engaging in contact sports in which the thumb is often contacted. As shown, the thumb protective device 1200 may include or be formed as a contoured member 1202 that is configured to cover at least a portion of the intended subject's thumb and hand. The contoured member 1202 may have an inner surface 1204 configured to face the thumb and an outer surface 1206 configured to face away from the thumb. The entirety of the inner surface 1204 may be configured to contact the subject's thumb or hand. In other words, the contoured member 1202 may be configured such that the inner surface 1204 form-fits to the subject's anatomy. FIGS. 13A-13H illustrate an example method for creating the thumb protective device 1200, which may be carried out in a manner as described above for the relevant anatomy.

Although the various protective devices described above may be provided contoured members formed as solid structures in some embodiments, alternative configurations of the contoured members may be used. For example, in some embodiments, the contoured members may be formed as, or may include, lattice structures having voids. The lattice structure, and the voids thereof, may in some instances provide force absorption when the device is impacted. In this manner, lattice structures may provide a greater degree of protection for the subject (e.g., as compared to non-lattice-based structures of previous approaches). For example, a contoured member or a portion thereof may have multiple layers including a solid, form-fitting layer contacting the subject's body, an adjacent layer formed as a lattice structure that allows energy to be absorbed. In some embodiments, the lattice structure may form the outer surface of the contoured member. In other embodiments, an additional solid, outer layer may be provided over the lattice structure layer. Various configurations of solid structures and lattice structures may be used for the devices.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed systems may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed system are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the system is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Aspects, features, and benefits of the claimed devices and methods for using the same will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the devices and methods for using the same to the precise forms disclosed. Many modifications and variations are possible in light of the above teaching.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

What is claimed is:

1. A protective device for protecting a protected location on a subject's body, the protective device comprising:
    a contoured member configured to cover at least a portion of the protected location, wherein the contoured member comprises:
    an outer profile surrounding an inner surface and an outer surface, wherein the outer profile is defined at least in part from anatomical data collected from the subject's body;
    the inner surface configured to face the protected location on the subject's body and at least partially conforming to the anatomical data;
    the outer surface configured to face away from the protected location;
    a first contact portion configured to contact the subject's body above the protected location;
    a second contact portion configured to contact the subject's body below the protected location; and
    a bridge portion positioned between the first contact portion and the second contact portion, wherein the bridge portion
        is configured to be offset from the protected location when the first contact portion and the second contact portion contact the subject's body.

2. The protective device of claim 1, wherein the first contact portion and the second contact portion are spaced apart from one another by the bridge portion.

3. The protective device of claim 1, wherein the bridge portion comprises a channel extending along the inner surface.

4. The protective device of claim 3, wherein at least a portion of the channel comprises a curved profile.

5. The protective device of claim 4, wherein a curvature of the curved profile varies along the at least a portion of the channel.

6. The protective device of claim 3, wherein the channel comprises a U-shaped profile.

7. The protective device of claim 6, wherein the bridge portion further comprises a ridge extending along the outer surface.

8. The protective device of claim 7, wherein the ridge comprises the curved profile.

9. The protective device of claim 7, wherein the ridge comprises the U-shaped profile.

10. The protective device of claim 1, wherein the contoured member comprises a thickness of about 4 mm.

11. The protective device of claim 1, wherein a magnitude of the offset is based at least in part on one or more peak points of the point cloud.

12. The protective device of claim 1, wherein the bridge portion comprises an Izod impact strength of about 70 J/m.

13. The protective device of claim 1, wherein the bridge portion comprises a flexural modulus of about 0.5 GPa.

14. The protective device of claim 1, wherein the inner surface is defined at least in part from a non-uniform rational basis (NURB)-spline surface modeling process.

15. The protective device of claim 1, wherein the anatomical data includes a boundary representation (BRep) solid modeling process performed on a point cloud.

16. A protective device for protecting a protected location on a subject's body, the protective device comprising:
    a contoured member configured to cover at least the protected location, wherein the contoured member comprises:
    an outer profile defined at least in part from anatomical data collected from the subject's body;
    an inner surface configured to face the protected location and at least partially conforming to the anatomical data, wherein the inner surface is defined at least in part from a non-uniform rational basis (NURB)-spline surface modeling process performed on the point cloud of anatomical data collected from the subject's body;
    an outer surface configured to face away from the protected location;
    a first contact portion configured to contact the subject's body above the protected location;
    a second contact portion configured to contact the subject's body below the protected location; and
    a bridge portion positioned between the first contact portion and the second contact portion, wherein the bridge portion
        does not contact the subject's body at the protected location when the first contact portion and the second contact portion contact the subject's body.

17. The protective device of claim 16, wherein the first contact portion and the second contact portion are spaced apart from one another by the bridge portion.

18. The protective device of claim 16, wherein the bridge portion comprises a channel extending along the inner surface.

19. The protective device of claim 18, wherein at least a portion of the channel comprises a curved profile.

20. The protective device of claim 19, wherein a curvature of the curved profile varies along the at least a portion of the channel.

21. The protective device of claim 18, wherein the channel comprises a U-shaped profile.

22. The protective device of claim 21, wherein the bridge portion further comprises a ridge extending along the outer surface.

23. The protective device of claim 22, wherein the ridge comprises the curved profile.

24. The protective device of claim 22, wherein the ridge comprises the U-shaped profile.

25. The protective device of claim 18, wherein the NURB-spline surface modeling process is performed on a point cloud of anatomical data collected from the subject's body.

26. The protective device of claim 16, wherein the outer profile surrounds the inner surface and the outer surface.

* * * * *